US008940877B2

(12) United States Patent
Bruckschwaiger et al.

(10) Patent No.: US 8,940,877 B2
(45) Date of Patent: *Jan. 27, 2015

(54) METHOD TO PRODUCE AN IMMUNOGLOBULIN PREPARATION WITH IMPROVED YIELD

(71) Applicants: Baxter International Inc., Deerfield, IL (US); Baxter Healthcare S.A., Glattpark (Opfikon) (CH)

(72) Inventors: Leopold Bruckschwaiger, Vienna (AT); Sonja Svatos, Berg (AT); Julia Nuernberger, Vienna (AT); Wolfgang Teschner, Vienna (AT); Harald Arno Butterweck, Vienna (AT); Hans-Peter Schwarz, Vienna (AT); Thomas Gundinger, Vienna (AT); Bernhard Koelbl, Achau (AT); Reinhard Grausenburger, Vienna (AT); Azra Pljevljakovic, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,332

(22) Filed: Oct. 16, 2012

(65) Prior Publication Data

US 2013/0101579 A1 Apr. 25, 2013

Related U.S. Application Data

(63) Continuation of application No. 12/789,365, filed on May 27, 2010.

(30) Foreign Application Priority Data

May 26, 2010 (AU) ................. 2010202125

(51) Int. Cl.
| | | |
|---|---|---|
| *A23J 1/00* | (2006.01) | |
| *C07K 1/00* | (2006.01) | |
| *C07K 14/16* | (2006.01) | |
| *C07K 16/00* | (2006.01) | |
| *C07K 17/00* | (2006.01) | |
| *C07K 1/36* | (2006.01) | |
| *A61K 9/00* | (2006.01) | |
| *A61K 9/08* | (2006.01) | |
| *A61K 35/16* | (2006.01) | |
| *A61K 47/18* | (2006.01) | |
| *C07K 1/30* | (2006.01) | |
| *C07K 16/06* | (2006.01) | |
| *A61K 38/17* | (2006.01) | |
| *C07K 1/14* | (2006.01) | |
| *C07K 1/34* | (2006.01) | |
| *C07K 1/18* | (2006.01) | |

(52) U.S. Cl.
CPC ................. *C07K 1/36* (2013.01); *A61K 9/0019* (2013.01); *A61K 9/08* (2013.01); *A61K 35/16* (2013.01); *A61K 47/183* (2013.01); *C07K 1/30* (2013.01); *C07K 16/065* (2013.01); *A61K 38/1709* (2013.01); *C07K 1/14* (2013.01); *C07K 1/34* (2013.01); *C07K 1/18* (2013.01)
USPC ........................... 530/412; 530/418; 530/424

(58) Field of Classification Search
None
See application file for complete search history.

(56) References Cited

U.S. PATENT DOCUMENTS

| | | |
|---|---|---|
| 3,998,946 A | 12/1976 | Condie et al. |
| 4,056,614 A | 11/1977 | Bonneau et al. |
| 4,136,094 A | 1/1979 | Condie |
| 4,216,205 A | 8/1980 | Radowitz |
| 4,378,346 A * | 3/1983 | Tankersley ................... 514/15.3 |
| 4,499,073 A | 2/1985 | Tenold |
| 4,550,019 A | 10/1985 | Polson |
| 5,061,237 A | 10/1991 | Gessler et al. |
| 5,122,373 A | 6/1992 | Eibl et al. |
| 5,130,451 A | 7/1992 | Pourreau et al. |
| 5,136,094 A | 8/1992 | Listemann et al. |
| 5,177,194 A | 1/1993 | Sarno et al. |
| 5,324,425 A | 6/1994 | Ellison |
| 5,886,154 A | 3/1999 | Lebing et al. |
| 6,069,236 A | 5/2000 | Burnouf-Radosevich et al. |

(Continued)

FOREIGN PATENT DOCUMENTS

| | | |
|---|---|---|
| DE | 3523615 A1 | 1/1987 |
| DE | 100 08 619 A1 | 9/2011 |

(Continued)

OTHER PUBLICATIONS

Buchacher et al. "Purification of intravenous immunoglobulin G from human plasma—aspects of yield and virus safety" Biotechnol. J. 2006, 1, 148-163.*

(Continued)

*Primary Examiner* — Daniel E Kolker
*Assistant Examiner* — James Rogers
(74) *Attorney, Agent, or Firm* — Morgan, Lewis & Bockius LLP

(57) ABSTRACT

The present invention provides improved methods for the manufacturing of IVIG products. These methods offer various advantages such as reduced loss of IgG during purification and improved quality of final products. In other aspects, the present invention provides aqueous and pharmaceutical compositions suitable for intravenous, subcutaneous, and/or intramuscular administration. In yet other embodiments, the present invention provides methods of treating a disease or condition comprising administration of an IgG composition provided herein.

27 Claims, 10 Drawing Sheets

(56) References Cited

U.S. PATENT DOCUMENTS

| | | | |
|---|---|---|---|
| 6,093,324 A * | 7/2000 | Bertolini et al. | 210/635 |
| 6,124,437 A | 9/2000 | Hirao et al. | |
| 6,159,471 A | 12/2000 | Hirao et al. | |
| 6,835,379 B2 | 12/2004 | Andersson et al. | |
| 7,186,410 B2 | 3/2007 | Chtourou et al. | |
| 7,553,938 B2 | 6/2009 | Buchacher et al. | |
| 8,304,524 B2 | 11/2012 | Bairstow et al. | |
| 2002/0098182 A1 | 7/2002 | Weisbart et al. | |
| 2002/0114802 A1 | 8/2002 | Tjellstrom et al. | |
| 2003/0099635 A1 | 5/2003 | Barstow et al. | |
| 2007/0020647 A1 | 1/2007 | Hageman et al. | |
| 2008/0318841 A1 | 12/2008 | Chtourou et al. | |
| 2009/0118163 A1 | 5/2009 | Gronski et al. | |
| 2009/0148463 A1 | 6/2009 | Reipert et al. | |
| 2009/0203580 A1 | 8/2009 | Dinarello et al. | |
| 2010/0330071 A1 | 12/2010 | Teschner et al. | |
| 2011/0021432 A1 | 1/2011 | Bairstow et al. | |

FOREIGN PATENT DOCUMENTS

| | | |
|---|---|---|
| EP | 0 222 611 A2 | 5/1987 |
| EP | 0 440 509 A2 | 8/1991 |
| EP | 0 893 450 A1 | 1/1999 |
| GB | 1 344 340 | 9/1972 |
| SE | 348 942 | 9/1972 |
| WO | WO 99/43362 A1 | 9/1999 |
| WO | WO 2005/026197 A1 | 3/2005 |
| WO | WO 2005/073252 A1 | 8/2005 |
| WO | WO 2007/038995 A1 | 4/2007 |
| WO | WO 2007/066017 A2 | 6/2007 |
| WO | WO 2007/066017 A3 | 6/2007 |
| WO | WO 2007/085626 A1 | 8/2007 |
| WO | WO 2008/113589 A1 | 9/2008 |

OTHER PUBLICATIONS

Ahrer et al. "Effects of ultra-/diafiltration conditions on present aggregates in human immunoglobulin G preparations" J. Membrane Science 274 (2006) 108-115.*

Barandun, S. et al., "Intravenous Administration of Human γ-Globulin," Vox Sanguinis, 1962, pp. 157-174, vol. 7.

Bee, W.H. et al., "Effects of Recombinant Human Hyaluronidase (rHuPH20) on Subcutaneous Administration of 10% and 20% IgC in Yucatan Mini Pigs," J. Allergy Clin. Immunol., Feb. 2010, 2 pages (p. Abstracts AB139), Abstract No. 547, vol. 125, No. 2, Suppl 2.

Cohn, E.J. et al., "Preparation and Properties of Serum and Plasma Proteins. IV. A System for the Separation into Fractions of the Protein and Lipoprotein Components of Biological Tissues and Fluids," J. Am. Chem. Soc., Mar. 1946, pp. 459-475, vol. 68, No. 3.

Curling, J.M. ed., Methods of Plasma Protein Factionation, 1980, Academic Press, pp. 12-13, 248-249, Table 1.

Falksveden, L.-G, et al., "Ion Exchange and Polyethylene Glycol Precipitation of Immunoglobulin G," in Methods of Plasma Protein Fractionation, Curling, J.M. ed., 1980, pp. 93-103, Academic Press, New York, NY.

Gun'Ko, V.M. et al., "Aqueous Suspensions of Furned Silica and Adsorption of Proteins," Journal of Colloid and Interface Science, 1997, vol. 192, pp. 166-178.

Hermann, C. et al., "Analysis of Fc-Receptor-Mediated Activities of New IgG Products Using a Novel THP-1 Cell-based Assay," J. Allergy Clin. Immunol., Feb. 2010, 2 pages (p. Abstracts (AB79), Abstract No. 312, vol. 125, No. 2, Suppl 1.

Hofmeister, Y. et al., "Human IgG Subclasses: In Vitro Neutralization of and In Vivo Protection against West Nile Virus," Journal of Virology, Feb. 2011, pp. 1896-1899, vol. 85, No. 4.

International Search Report mailed on Apr. 2, 2012, for International Patent Application No. PCT/US2011/038247 filed May 26, 2011, 3 pages.

Koblet, H. et al., "Turnover of Standard-Gammaglobulin, pH-4-Gammaglobulin and Pepsin Desaggregated Gammaglobulin and Clinical Implications," Vox Sanguinis, 1967, pp. 93-102, vol. 13.

Kreil, T.R. et al., "Development of a New 10% Liquid, Triple Virus Reduced Intra-venous Immune-Globulin Product, New Generation IGIV," J. Allergy Clin Immunol., Feb. 2004, p. S128 Abstracts. Abstract No. 410.

Kreil, T.R. et al., "Pathogen Safety Profile of a New 10% Liquid, Triple Virus Reduced Intravenous Immune Globulin Product, New Generation IGIV (NG IGIV)—Further Studies," J. Allow Clin. Immunol., Feb. 2005, p. S156 Abstracts, Abstract No. 623.

Kreil, T.R. et al., "Removal of small nonenveloped viruses by antibody-enchanced nanofiltration during the manufacture of plasma derivatives," Transfusion, Jul. 2006, pp. 1143-1151, vol. 46.

Lebing, W. et al., "Properties of a new intravenous immunoglobulin (IGIV-C, 10%) produced by virus inactivation with caprylate and column chromatography," Vox Sanguinis, 2003, pp. 193-201, vol. 84.

Leesch, V.W. et al., "30-Day Pharmacokinetic Evaluation of IV versus Subcutaneous Administration of Immunoglobulin with and without Recombinant Human Hyaluronidase in Dogs." J. Allergy Clin. Immunol., Feb. 2009, p. S10 Abstracts, Abstract No. 24.

Nitschmann, H., et al., "Vereinfachtes Verfahren zur Gewinnung von Humanem Albumin and Gamma-Globulin aus Blutplasma Mittels Alkoholfaellung," Helvetica Chimica Acta, Verlag Helvetica Chimica Acta, vol. 37, Jan. 1, 1954, pp. 866-873.

Olas, K. et al., "Immunomodulatory properties of human serum immunoglobulin A: anti-inflammatory and pro-inflammatory activities in human monocytes and peripheral blood mononuclear cells," Clinical and Experimental Immunology, 2005, pp. 478-490, vol. 140.

Olas, K. et al., "Natural anti-amyloid beta antibodies in intravenous immunoglobulin prevent amyloid beta-induced neurotoxicity in vitro," Immunology, 2008, p. 19, Abstract No. 3.5, vol. 125, Suppl 1.

Oncley, J.L et al., "The Separation of the Antibodies, Isoagglutinins, Prothrombin, Plasminogen and $β_1$-Lipoprotein into Subfractions of Human Plasma," J. Am. Chem. Soc., Feb. 1949, pp. 541-550, vol. 71.

Poelsler, G. et al., "A new liquid intravenous immunoglobulin with three dedicated virus reduction steps: virus and prion reduction capacity," Vox Sanguinis, 2007, pp. 1-9.

Reipert, B.M. et al., "Evaluating the Fc-Function of Intravenous Immunoglobulin Products by Flow Cytometry," J. Allergy Clin. Immunol., Feb. 2004, p. S214 Abstracts, Abstract No. 751.

Reipert, B.M. et al., "Fc function of a new intravenous immunoglobulin product: IGIV 10% triple virally inactivated solution," Vox Sanguinis, 2006, pp. 256-263, vol. 91.

Tanaka, K. et al., "High quality human immunoglobulin G purified from Cohn fractions by liquid chromatography," Brazilian Journal of Medical and Biological Research, 2000, pp. 27-30, vol. 33, No. 1.

Teschner, IV, W. et al., "Preclinical Characterization of a New Liquid 'Immune Globulin Intravenous (Human), 10% Triple Virally Reduced Solution' (IGIV, 10%TVR)," J. Allergy Clin. Immunol., Feb. 2004, 2 pages, (p. Abstracts S45), Abstract No. 79, vol. 113, No. 2, Suppl. 1.

Teschner, W. et al., "A new liquid, intravenous immunoglobulin product (IGIV 10%) highly purified by a state-of-the-art process," Vox Sanguinis, 2007, pp. 42-55, vol. 92.

Weber, A. et al., "Intravenous Immunoglobulin (IVIG) Gammagard Liquid Contains Anti-Rage IGG and SLRP," Alzheimer's & Dementia: The Journal of the Alzheimer's Association, Jul. 2009, 3 pages (p. P416), Abstract No. P3-248, vol. 5, No. 4, Suppl.

Cammarata, P.S. et al., "Fractionation and Properties of Glutamic-Oxalacetic Transaminase," The Journal of Biological Chemistry, Nov. 1951, vol. 193, No. 1, pp. 53-62.

Goldsmith, et al., "The Activation of Plasminogen by Hagemen Factor (Factor XII) and Hageman Factor Fragments," J. Clin. Invest/, 1978, 62,(1), pp. 54-60.

Guerffroy, "A guide for the preparation and use of buffers in biological systems," © 1975 by Behring Diagnostics, pp. 1-25.

Material Safety Data Sheet #2402, revised Jun. 30, 2012, pp. 1-2.

Schultze, H.E. et al., Molecular Biology of Human Proteins, vol. 1: Nature and Metabolism of Extracellular Proteins, 1966, Elsevier Publishing Company, pp. 236-317.

* cited by examiner

METHOD TO PRODUCE AN IMMUNOGLOBULIN PREPARATION WITH IMPROVED YIELD

CROSS-REFERENCES TO RELATED APPLICATIONS

This application is a continuation of U.S. patent application Ser. No. 12/789,365, filed May 27, 2010, which claims priority to Australian application number 2010202125, filed May 26, 2010, which are hereby incorporated herein by reference in its entirety for all purposes.

BACKGROUND OF THE INVENTION

Immune globulin products from human plasma were first used in 1952 to treat immune deficiency. Initially, intramuscular or subcutaneous administration of Immunoglobulin isotype G (IgG) were the methods of choice. For injecting larger amounts of IgG necessary for effective treatment of various diseases, however, the intravenous administrable products with lower concentrated IgG (50 mg/mL) were developed. Usually intravenous immunoglobulin (IVIG), contains the pooled immunoglobulin G (IgG) immunoglobulins from the plasma of more than a thousand blood donors. Typically containing more than 95% unmodified IgG, which has intact Fc-dependent effector functions, and only trace amounts of immunoglobulin A (IgA) or immunoglobulin M (IgM), IVIGs are sterile, purified IgG products primarily used in treating three main categories of medical conditions: (1) immune deficiencies such as X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Specifically, many people with primary immunodeficiency disorders lack antibodies needed to resist infection. In certain cases these deficiencies can be supplemented by the infusion of purified IgG, commonly through intravenous administration (i.e., IVIG therapy). Several primary immunodeficiency disorders are commonly treated in the fashion, including X-linked Agammaglobulinemia (XLA), Common Variable Immunodeficiency (CVID), Hyper-IgM Syndrome (HIM), Severe Combined Immunodeficiency (SCID), and some IgG subclass deficiencies (Blaese and Winkelstein, J. Patient & Family Handbook for Primary Immunodeficiency Diseases. Towson, Md.: Immune Deficiency Foundation; 2007).

While IVIG treatment can be very effective for managing primary immunodeficiency disorders, this therapy is only a temporary replacement for antibodies that are not being produced in the body, rather than a cure for the disease. Accordingly, patients dependent upon IVIG therapy require repeated doses, typically about once a month for life. This need places a great demand on the continued production of IVIG compositions. However, unlike other biologics that are produced via in vitro expression of recombinant DNA vectors, IVIG is fractionated from human blood and plasma donations. Thus, IVIG products cannot be increased by simply increasing the volume of production. Rather the level of commercially available IVIG is limited by the available supply of blood and plasma donations.

Several factors drive the demand for IVIG, including the acceptance of IVIG treatments, the identification of additional indications for which IVIG therapy is effective, and increasing patient diagnosis and IVIG prescription. Notably, the global demand for IVIG has more than quadrupled since 1990 and continues to increase today at an annual rate between about 7% and 10% (Robert P., *Pharmaceutical Policy and Law*, 11 (2009) 359-367). For example, the Australian National Blood Authority reported that the demand for IVIG in Australia grew by 10.6% for the 2008-2009 fiscal year (National Blood Authority Australia Annual Report 2008-2009).

Due in part to the increasing global demand and fluctuations in the available supply of immunoglobulin products, several countries, including Australia and England, have implemented demand management programs to protect supplies of these products for the highest demand patients during times of product shortages.

It has been reported that in 2007, 26.5 million liters of plasma were fractionated, generating 75.2 metric tons of IVIG, with an average production yield of 2.8 grams per liter (Robert P., supra). This same report estimated that global IVIG yields are expected to increase to about 3.43 grams per liter by 2012. However, due to the continued growth in global demand for IVIG, projected at between about 7% and 13% annually between now and 2015, further improvement of the overall IVIG yield will be needed to meet global demand.

A number of IVIG preparation methods are used by commercial suppliers of IVIG products. One common problem with the current IVIG production methods is the substantial loss of IgG during the purification process, estimated to be at least 30% to 35% of the total IgG content of the starting material. One challenge is to maintain the quality of viral inactivation and lack of impurities which can cause adverse reactions, while bolstering the yield of IgG. At the current production levels of IVIG, what may be considered small increases in the yield are in fact highly significant. For example at 2007 production levels, a 2% increase in efficiency, equal to an additional 56 milligrams per liter, would generate 1.5 additional metric tons of IVIG.

In the fourth installment of a series of seminal papers published on the preparation and properties of serum and plasma proteins, Cohn et al. (*J. Am. Chem. Soc.*, 1946, 68(3): 459-475) first described a methods for the alcohol fractionation of plasma proteins (method 6), which allows for the isolation of a fraction enriched in IgG from human plasma. Several years later, Oncley et al. (*J. Am. Chem. Soc.*, 1949, 71(2): 541-550) expanded upon the Cohn methods by publishing a method (method 9) that resulted in the isolation of a purer IgG preparation.

These methods, while laying the foundation for an entire industry of plasma derived blood factors, were unable to provide IgG preparations having sufficiently high concentrations for the treatment of several immune-related diseases, including Kawasaki syndrome, immune thrombocytopenic purpura, and primary immune deficiencies. As such, additional methodologies employing various techniques, such as ion exchange chromatography, were developed to provide higher purity and higher concentration IgG formulations. Hoppe et al. (*Munch Med Wochenschr* 1967 (34): 1749-1752) and Falksveden (Swedish Patent No. 348942) and Falksveden and Lundblad (*Methods of Plasma Protein Fractionation* 1980) were among the first to employ ion exchange chromatography for this purpose.

Various modern methods employ a precipitation step, such as caprylate precipitation (Lebing et al., *Vox Sang* 2003 (84): 193-201) and Cohn Fraction (I+)II+III ethanol precipitation (Tanaka et al., *Braz J Med Biol Res* 2000 (33)37-30) coupled to column chromatography. Most recently, Teschner et al. (*Vox Sang*, 2007 (92):42-55) have described a method for production of a 10% IVIG product in which cryo-precipitate is first removed from pooled plasma and then a modified Cohn-Oncley cold ethanol fractionation is performed, followed by S/D treatment of the intermediate, ion exchange chromatography, nanofiltration, and optionally ultrafiltration/diafiltration.

However, despite the improved purity, safety, and yield afforded by these IgG manufacturing methods, a significant amount of IgG is still lost during the purification process. For example, Teschner et al. report that their method results in an increased IgG yield of 65% (Teschner et al., supra). As reported during various plasma product meetings, the average yields for large-scale preparation of IgG, such as from Baxter, CSL Behring, Upfront Technology, Cangene, Prometric Bio-Therapeutics, and the Finnish Red Cross, range from about 61% to about 65% in the final container. This represents a loss of at least about a third of the IgG present in the pooled plasma fraction during the manufacturing process.

As such, a need exists for improved and more efficient methods for manufacturing IVIG products. The present invention satisfies these and other needs by providing IVIG manufacturing methods that produce yields that are at least 6 to 10% higher than currently achievable, as well as IVIG compositions provided there from.

BRIEF SUMMARY OF THE INVENTION

In one aspect, the present invention provides methods for preparing an enriched IgG compositions (e.g., IVIG compositions) from plasma. Advantageously, the methods provided herein provide significant improvements over current state of the art manufacturing methods for preparing IVIG compositions. For example, the methods provided herein allow for increased yields of IgG in the final bulk composition without losing the purity required for intravenous administration.

In one aspect, a method is provided for preparing an enriched IgG composition from plasma comprising the steps of (a) precipitating a cryo-poor plasma fraction, in a first precipitation step, with between about 6% and about 10% alcohol at a pH of between about 7.0 and about 7.5 to obtain a first precipitate and a first supernatant, (b) precipitating IgG from the first supernatant, in a second precipitation step, with between about 20% and about 25% alcohol at a pH of between about 6.7 and about 7.3 to form a second precipitate, (c) re-suspending the second precipitate to form a suspension, (d) precipitating IgG from the suspension formed in step (c), in a third precipitation step, with between about 22% and about 28% alcohol at a pH of between about 6.7 and about 7.3 to form a third precipitate, (e) re-suspending the third precipitate to form a suspension, and (0 separating the soluble fraction from the suspension formed in step (e), thereby forming an enriched IgG composition, wherein at least one of the first precipitation step, second precipitation step, or third precipitation step comprises spray addition of the alcohol. In one embodiment, alcohol is added in the first precipitation step by spraying. In another embodiment, alcohol is added in the second precipitation step by spraying. In yet another embodiment, alcohol is added in the third precipitation step by spraying.

In certain embodiments, the pH of one or more solution may be adjusted by the addition of a pH modifying agent by spraying. In related embodiments, the pH of at least one of the first precipitation step, second precipitation step, or third precipitation step is achieved by addition of a pH modifying solution after addition of the alcohol, or before and after the addition of alcohol, during and after the addition of alcohol, or before, during, and after the addition of alcohol. In yet another related embodiment, the pH of a precipitation step may be maintained for the entirety of the precipitation reaction by continuously adjusting the pH.

In one specific embodiment, the pH of the first precipitation step is adjusted after the addition of alcohol by spray addition of a pH modifying agent. In another embodiment, the pH of the second precipitation step is adjusted after the addition of alcohol by spray addition of a pH modifying agent. In yet another embodiment, the pH of the third precipitation step is adjusted after the addition of alcohol by spray addition of a pH modifying agent.

Additionally, the preparatory methods provided herein may further comprise an ion exchange chromatography step (i.e., anion exchange and/or cation exchange chromatography), a nanofiltration step, an ultrafiltration/diafiltration step, or any other suitable purification technique to further enhance the purity or quality of the IVIG preparations.

In another aspect, a method is provided for preparing an enriched IgG composition from plasma comprising the steps of adjusting the pH of a cryo-poor plasma fraction to at or about 7.0, (b) adjusting the ethanol concentration of the cryo-poor plasma fraction of step (a) to at or about 25% (v/v) at a temperature between at or about –7° C. and at or about –9° C., thereby forming a mixture, (c) separating liquid and precipitate from the mixture of step (b), (d) re-suspending the precipitate of step (c) with a buffer containing phosphate and acetate, wherein the pH of the buffer is adjusted with at or about 600 ml of glacial acetic acid per 1000 L of buffer, thereby forming a suspension, (e) mixing finely divided silicon dioxide ($SiO_2$) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with at or about 150 ml of glacial acetic acid per 1000 L of buffer, thereby forming a wash solution, (h) combining the filtrate of step (0 with the wash solution of step (g), thereby forming a solution, and treating the solution with a detergent, (i) adjusting the pH of the solution of step (h) to at or about 7.0 and adding ethanol to a final concentration of at or about 25%, thereby forming a precipitate, (j) separating liquid and precipitate from the mixture of step (i), (k) dissolving the precipitate in an aqueous solution comprising a solvent or detergent and maintaining the solution for at least 60 minutes, (1) passing the solution after step (k) through a cation exchange chromatography column and eluting proteins absorbed on the column in an eluate, (m) passing the eluate from step (l) through an anion exchange chromatography column to generate an effluent, (n) passing the effluent from step (m) through a nanofilter to generate a nanofiltrate, (o) passing the nanofiltrate from step (n) through an ultrafiltration membrane to generate an ultrafiltrate; and (p) diafiltrating the ultrafiltrate from step (o) against a diafiltration buffer to generate a diafiltrate having a protein concentration between about 8% (w/v) and about 12% (w/v), thereby obtaining a composition of concentrated IgG.

In another aspect, the present invention provides aqueous IgG compositions prepared by the methods described herein. Generally, the IgG compositions have high purity (e.g., at least 95%, 98%, 99%, or higher IgG contents), contain protein concentrations between about 20 g/L and about 200 g/L, and contain extremely low levels of common IVIG contaminants, such as IgG, IgM, Fibrinogen, Transferrin, ACA, amidolytic activity, PKA, and the like.

In yet another aspect, pharmaceutical IgG compositions and formulations suitable for use in IVIG therapies are provided. The pharmaceutical formulations have high purity (e.g., at least 98%, 99%, or higher IgG contents), contain protein concentrations between about 20 g/L and about 200 g/L, and contain extremely low levels of common IVIG contaminants, such as IgG, IgM, Fibrinogen, Transferrin, ACA, amidolytic activity, PKA, and the like. Generally, the pharmaceutical compositions are appropriately formulated for intravenous administration (i.e., for IVIG therapy), subcutaneous administration, or intramuscular administration.

In another aspect, the present invention provides methods for treating an immunodeficiency, autoimmune disease, or acute infection in a human in need thereof, the method comprising administering a pharmaceutical composition described herein. Non, limiting examples of diseases and conditions that may be treated or managed through the methods provided herein include, allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), kidney transplant with a high antibody recipient or with an ABO incompatible donor, chronic fatigue syndrome, *clostridium difficile* colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, hypogammaglobulinemia, primary immune deficiency, RRMS, Alzheimer's disease, and Parkinson's disease.

DEFINITIONS

Figure 1:
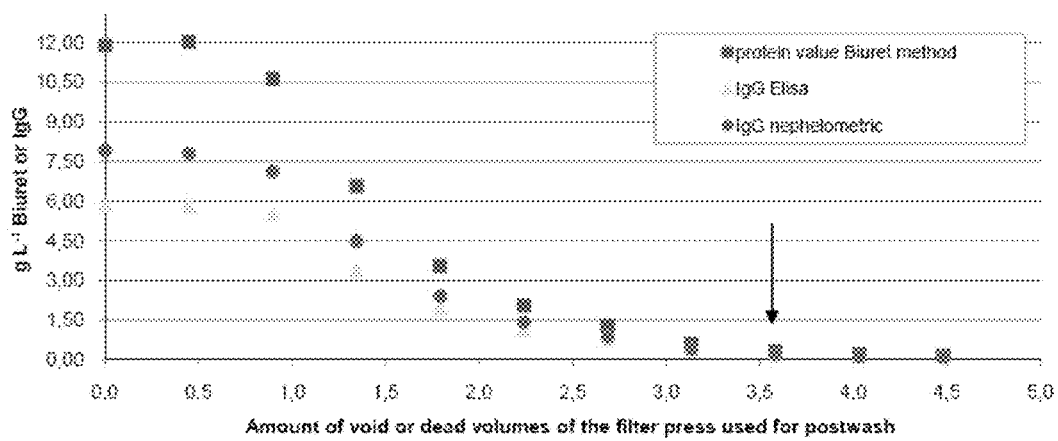
FIG. 1: IgG concentration as determined by ELISA (▲) and nephelometric (•) methods and total protein concentration (■) present in the Fraction II+III filtrate wash as a function of the number of dead volumes of buffer used to wash the filtration device post-filtration.

As used herein, an "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating colloids like proteins from small molecules like sugars and salts.

As used herein, the term "diafiltration" is performed with the same membranes as ultrafiltration and is a tangential flow filtration. During diafiltration, buffer is introduced into the recycle tank while filtrate is removed from the unit operation. In processes where the product is in the retentate (for example IgG), diafiltration washes components out of the product pool into the filtrate, thereby exchanging buffers and reducing the concentration of undesirable species.

As used herein, the term "about" denotes an approximate range of plus or minus 10% from a specified value. For instance, the language "about 20%" encompasses a range of 18-22%.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the term "Intravenous IgG" or "IVIG" treatment refers generally to a therapeutic method of intravenously, subcutaneously, or intramuscularly administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titres for specific antigens (e.g., Rho D factor, pertussis toxin, tetanus toxin, botulism toxin, rabies, etc.). For ease of discussion, such subcutaneously or intramuscularly formulated IgG compositions are also included in the term "IVIG" in this application.

By "therapeutically effective amount or dose" or "sufficient/effective amount or dose," it is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: The Science and Practice of Pharmacy, 20th Edition, 2003, Gennaro, Ed., Lippincott, Williams & Wilkins).

As used in this application, the term "spraying" refers to a means of delivering a liquid substance into a system, e.g., during an alcohol precipitation step, such as a modified Cohn fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

DETAILED DESCRIPTION OF THE INVENTION

I. Overview

As routinely practiced in modern medicine, sterilized preparations of concentrated immunoglobulins (especially IgGs) are used for treating medical conditions that fall into three main classes: immune deficiencies, inflammatory and autoimmune diseases, and acute infections. One commonly used IgG product, intravenous immunoglobulin or IVIG, is formulated for intravenous administration, for example, at a concentration of at or about 10% IgG. Concentrated immunoglobulins may also be formulated for subcutaneous or intramuscular administration, for example, at a concentration at or about 20% IgG. For ease of discussion, such subcutaneously or intramuscularly formulated IgG compositions are also included in the term "IVIG" in this application.

In certain aspects, the present invention provides methods for IVIG manufacture that increase the final yield of the product, yet still provide IVIG compositions of equal or higher quality and in some cases higher concentrations. In one embodiment, the present invention provides modified Cohn fractionation methods that reduce IgG loss at one or more precipitation steps.

In another aspect, the present invention provides IgG compositions prepared according to the improved manufacturing methods provided herein. Advantageously, these compositions are less expensive to prepare than commercial products currently available due to the improved yield afforded by the methods provided herein. Furthermore, these compositions are as pure, if not more pure, than compositions manufactured using commercial methods Importantly, these compositions are suitable for use in IVIG therapy for immune deficiencies, inflammatory and autoimmune diseases, and acute infections. In one embodiment, the IgG composition is at or about 10% IgG for intravenous administration. In another embodiment, the IgG composition is at or about 20% for subcutaneous or intramuscular administration.

In another aspect, the present invention provides pharmaceutical compositions and formulations of IgG compositions prepared according to the improved manufacturing methodologies provided herein. In certain embodiments, these compositions and formulations provide improved properties as compared to other IVIG compositions currently on the market. For example, in certain embodiments, the compositions and formulations provided herein are stable for an extended period of time.

In yet another aspect, the present invention provides method for treating immune deficiencies, inflammatory and autoimmune diseases, and acute infections comprising the administration of an IgG composition prepared using the improved methods provided herein.

II. Methods of IVIG Manufacture

Generally, immunoglobulin preparations according to the present invention can be prepared from any suitable starting materials, for example, recovered plasma or source plasma. In a typical example, blood or plasma is collected from healthy donors. Usually, the blood is collected from the same species of animal as the subject to which the immunoglobulin preparation will be administered (typically referred to as "homologous" immunoglobulins). The immunoglobulins are isolated from the blood by suitable procedures, such as, for example, precipitation (alcohol fractionation or polyethylene glycol fractionation), chromatographic methods (ion exchange chromatography, affinity chromatography, immunoaffinity chromatography, etc.) ultracentrifugation, and electrophoretic preparation, and the like. (See, e.g., Cohn et al., *J. Am. Chem. Soc.* 68:459-75 (1946); Oncley et al., *J. Am. Chem. Soc.* 71:541-50 (1949); Barundern et al., *Vox Sang.* 7:157-74 (1962); Koblet et al., *Vox Sang.* 13:93-102 (1967); U.S. Pat. Nos. 5,122,373 and 5,177,194; the disclosures of which are hereby incorporated by reference in their entireties for all purposes).

In many cases, immunoglobulins are prepared from gamma globulin-containing products produced by alcohol fractionation and/or ion exchange and affinity chromatography methods well known to those skilled in the art. For example, purified Cohn Fraction II is commonly used as a starting point for the isolation of immunoglobulins. The starting Cohn Fraction II paste is typically about 95 percent IgG and is comprised of the four IgG subtypes. The different subtypes are present in Fraction II in approximately the same ratio as they are found in the pooled human plasma from which they are obtained. The Fraction II is further purified before formulation into an administrable product. For example, the Fraction II paste can be dissolved in a cold purified aqueous alcohol solution and impurities removed via precipitation and filtration. Following the final filtration, the immunoglobulin suspension can be dialyzed or diafiltered (e.g., using ultrafiltration membranes having a nominal molecular weight limit of less than or equal to 100,000 daltons) to remove the alcohol. The solution can be concentrated or diluted to obtain the desired protein concentration and can be further purified by techniques well known to those skilled in the art.

Furthermore, additional preparative steps can be used to enrich a particular isotype or subtype of immunoglobulin. For example, protein A, protein G or protein H sepharose chromatography can be used to enrich a mixture of immunoglobulins for IgG, or for specific IgG subtypes. See generally Harlow and Lane, *Using Antibodies*, Cold Spring Harbor Laboratory Press (1999); Harlow and Lane, *Antibodies, A Laboratory Manual*, Cold Spring Harbor Laboratory Press (1988); and U.S. Pat. No. 5,180,810, the disclosures of which are hereby incorporated by reference in their entireties for all purposes.

Unlike the methods described above, in one aspect the present invention provides methods of preparing concentrated IgG compositions that utilize a cryo-poor starting material. Generally, the methods provided herein utilize both modified Cohn-Oncley alcohol fractionation steps and ion exchange chromatography to provide superior IgG yields, while maintaining the same, if not improved, quality as found in currently available commercial IVIG preparations. For example, in certain embodiments methods are provided that yield a final bulk IgG composition containing close to 75% of the IgG content found in the raw plasma starting material. These methods represent at least a 10% to 12% increase in the overall IgG yield over existing state of the art purification methods. For example, it is estimated that the GAMMA-GARD® LIQUID manufacturing process provide a final yield of between about 60% and 65% of the IgG content found in the starting material. As such, the methods provided herein provide a significant improvement over the existing IgG purification technologies.

In one embodiment, the present invention provides a purified IgG composition that contains at least 70% of the IgG content found in the raw plasma starting material. In another embodiment, a purified IgG composition is provided that contains at least 75% of the IgG content found in the raw plasma starting material. In other embodiments, a purified IgG composition provided herein will contain at least about 65% of the IgG content found in the raw plasma starting material, or at least 66%, 67%, 68%, 69%, 70%, 71%, 72%73%, 74%, 75%, or more of the IgG content found in the raw plasma starting material.

A. Modified Alcohol Precipitation/Ion Exchange Chromatography Fractionation Methods In one aspect, the present invention provides improved methods for the manufacture of IgG compositions suitable for use in IVIG therapy. Generally, these methods provide IgG preparations having higher yields and comparable if not higher purity than current methods employed for the production of commercial IVIG products.

In one specific aspect, the present invention provides a method for preparing a composition of concentrated IgG from plasma, e.g., 10% IVIG, the method comprising performing at least one alcohol precipitation step and at least one ion exchange chromatography step. In particular, several steps in the improved upstream process are different from prior processes, e.g., the use of 25% ethanol at lower temperatures, ethanol addition by spraying, pH adjustment by spraying, and the use of finely divided silica particles.

In a certain embodiment, the method comprises the steps of (a) precipitating a cryo-poor plasma fraction, in a first precipitation step, with between about 6% and about 10% alcohol at a pH of between about 6.7 and about 7.3 to obtain a supernatant enriched in IgG, (b) precipitating IgG from the supernatant with between about 20% and about 30% alcohol at a lower temperature and at a pH of between about 6.7 and about 7.3 to form a first precipitate, (c) re-suspending the first precipitate formed in step (b) to form a suspension, (d) treating the suspension formed in step (c) with a detergent, (e) precipitating IgG from the suspension with between about 20% and about 30% alcohol at a pH of between about 6.7 and about 7.3 to form a second precipitate, (f) re-suspending the second precipitate formed in step (e) to form a suspension, (g) treating the suspension formed in step (f) with a solvent and/or detergent, and (h) performing at least one ion exchange chromatography fractionation thereby preparing a composition of concentrated IgG. In one embodiment, the method further comprises treating the suspension formed in step (c) with finely divided silica dioxide ($SiO_2$) and filtering the solution prior to step (d).

In one embodiment, a method for preparing a concentrated IgG composition from plasma is provided, the method comprising the steps of (a) adjusting the pH of a cryo-poor plasma fraction to about 7.0, (b) adjusting the ethanol concentration of the cryo-poor plasma fraction of step (a) to at or about 25% (v/v) at a temperature between about −5° C. and about −9° C., thereby forming a mixture, wherein the ethanol concentration may be adjusted by spraying, (c) separating liquid and precipitate from the mixture of step (b), (d) re-suspending the precipitate of step (c) with a buffer containing phosphate and acetate, wherein the pH of the buffer is adjusted with between about 400 and about 700 ml of glacial acetic acid per 1000 L of buffer, thereby forming a suspension, (e) mixing finely divided silicon dioxide (SiO2) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with about 150 ml of glacial acetic acid per 1000 L of buffer, thereby forming a wash solution, (h) combining the filtrate of step (f) with the wash solution of step (g), thereby forming a solution, and treating the solution with a detergent, (i) adjusting the pH of the solution of step (h) to about 7.0 and adding ethanol to a final concentration of at or about 25%, thereby forming a precipitate, wherein the ethanol concentration and/or pH may be adjusted by spraying (j) separating liquid and precipitate from the mixture of step (i), (k) dissolving the precipitate in an aqueous solution comprising a solvent or detergent and maintaining the solution for at least 60 minutes, (l) passing the solution after step (k) through a cation exchange chromatography column and eluting proteins absorbed on the column in an eluate, (m) passing the eluate from step (l) through an anion exchange chromatography column to generate an effluent (i.e., flow-through), (n) passing the effluent from step (m) through a nanofilter to generate a nanofiltrate, (o) passing the nanofiltrate from step (n) through an ultrafiltration membrane to generate an ultrafiltrate, and (p) diafiltrating the ultrafiltrate from step (o) against a diafiltration buffer to generate a diafiltrate having a protein concentration between about 8% (w/v) and about 22% (w/v), thereby obtaining a composition of concentrated IgG. In one embodiment, the temperature of step (b) is at or about −7° C. In one specific embodiment, the suspension buffer in step (d) is adjusted with about 600 mL glacial acetic acid.

In certain embodiments, the diafiltrate will have a protein concentration between about 8% and about 12%, for example, about 8%, or about 9%, 10%, 11%, or 12%. In a preferred embodiment, the diafiltrate will have a protein concentration of at or about 10%. In another preferred embodiment, the diafiltrate will have a protein concentration of at or about 11%. In yet another preferred embodiment, the diafiltrate will have a protein concentration of at or about 12%. In other embodiments, the diafiltrate will have a protein concentration between about 13% and about 17%, for example, about 13%, or about 14%, 15%, 16%, or 17%. In yet other embodiments, the diafiltrate will have a protein concentration between about 18% and about 22%, for example, about 18%, or about 19%, 20%, 21%, or 22%. In a preferred embodiment, the diafiltrate will have a protein concentration of at or about 20%. In another preferred embodiment, the diafiltrate will have a protein concentration of at or about 21%. In yet another preferred embodiment, the diafiltrate will have a protein concentration of at or about 22%.

In certain embodiments of the present invention, the methods provided herein may comprise improvements in two or more of the fractionation process steps described above. For example, embodiments may include improvements in the first precipitation step, the Modified Fraction II+III precipitation step, the Modified Fraction II+III dissolution step, and/or the Modified Fraction II+III suspension filtration step.

In one embodiment, the improvement made in the first precipitation step is the addition of alcohol by spraying. In another embodiment, the improvement made in the first precipitation step is the addition of a pH modifying agent by spraying. In yet embodiment, the improvement made in the first precipitation step is the adjustment of the pH of the solution after addition of the alcohol. In a related embodiment, the improvement made in the first precipitation step is the maintenance of the pH during the addition of the alcohol. In another related embodiment, the improvement made in the first precipitation step is the maintenance of the pH during the precipitation incubation time by continuously adjusting the pH of the solution. In certain embodiments, the first precipitation step may be improved by implementing more than one of these improvements. Further improvements that may be realized in this step will be evident from the section provided below discussing the first precipitation step—Modified Fractionation I. By implementing one or more of the improvements described above, a reduced amount of IgG is lost in the precipitate fraction of the first precipitation step and/or a reduced fraction of IgG is irreversibly denatured during the precipitation step.

In one embodiment, the improvement made in the Modified Fraction II+III precipitation step is the addition of alcohol by spraying. In another embodiment, the improvement made in the Modified Fraction II+III precipitation step is the addition of a pH modifying agent by spraying. In yet embodiment, the improvement made in the Modified Fraction II+III precipitation step is the adjustment of the pH of the solution after addition of the alcohol. In a related embodiment, the improvement made in the Modified Fraction II+III precipitation step is the maintenance of the pH during the addition of the alcohol. In another related embodiment, the improvement made in the Modified Fraction II+III precipitation step is the maintenance of the pH during the precipitation incubation time by continuously adjusting the pH of the solution. In another aspect, the Modified Fraction II+III precipitation step is improved by increasing the concentration of alcohol to at or about 25%. In yet another embodiment, the Modified Fraction II+III precipitation step is improved by lowering the incubation temperature to between about −7° C. and −9° C. In certain embodiments, the Modified Fraction II+III precipitation step may be improved by implementing more than one of these improvements. Further improvements that may be realized in this step will be evident from the section provided below discussing the second precipitation step—Modified Fractionation II+III. By implementing one or more of the improvements described above, a reduced amount of IgG is lost in the supernatant fraction of the Modified Fraction II+III precipitation step and/or a reduced fraction of IgG is irreversibly denatured during the precipitation step.

In one embodiment, the improvement made in the Modified Fraction II+III dissolution step is achieved by increasing the glacial acetic acid content of the dissolution buffer to about 0.06%. In another embodiment, the improvement made in the Modified Fraction II+III dissolution step is achieved by maintaining the pH of the solution during the dissolution incubation time by continuously adjusting the pH of the solution. In another embodiment, the improvement made in the Modified Fraction II+III dissolution step is achieved by mixing finely divided silicon dioxide ($SiO_2$) with the Fraction II+III suspension prior to filtration. In certain embodiments, the Modified Fraction II+III dissolution step may be improved by implementing more than one of these improvements. Further improvements that may be realized in this step will be evident from the section provided below discussing the Modified Fraction II+III dissolution step—Extraction of the Modified Fraction II+III Precipitate. By implementing one or more of the improvements described above, an increased amount of IgG is recovered in the Fraction II+III suspension and/or the amount of impurities is reduced in the Fraction II+III suspension.

An exemplary improvement made in the Modified Fraction II+III suspension filtration step is realized by post-washing the filter with at least about 3.6 dead volumes of dissolution buffer containing at or about 150 mL glacial acetic acid per 1000 L. Further improvements that may be realized in this step will be evident from the section provided below discussing the Modified Fraction II+III suspension filtration step—Pretreatment and Filtration of the Modified Fraction II+III Suspension. By implementing one or more of the improvements described above, a reduced amount of IgG is lost during the Modified Fraction II+III suspension filtration step.

In one embodiment, the method may comprise an improvement in the first precipitation step and the Modified Fraction II+III precipitation step.

In another embodiment, the method may comprise an improvement in the first precipitation step and the Modified Fraction II+III dissolution step.

In another embodiment, the method may comprise an improvement in the first precipitation step and the Modified Fraction II+III suspension filtration step.

In another embodiment, the method may comprise an improvement in the Modified Fraction II+III precipitation step and the Modified Fraction II+III dissolution step.

In another embodiment, the method may comprise an improvement in the Modified Fraction II+III precipitation step and the Modified Fraction II+III suspension filtration step.

In another embodiment, the method may comprise an improvement in the Modified Fraction II+III dissolution step and the Modified Fraction II+III suspension filtration step.

In another embodiment, the method may comprise an improvement in the first precipitation step, the Modified Fraction II+III precipitation step, and the Modified Fraction II+III dissolution step.

In another embodiment, the method may comprise an improvement in the first precipitation step, the Modified Fraction II+III precipitation step, and the Modified Fraction II+III suspension filtration step.

In another embodiment, the method may comprise an improvement in the first precipitation step, the Modified Fraction II+III dissolution step, and the Modified Fraction II+III suspension filtration step.

In another embodiment, the method may comprise an improvement in the Modified Fraction II+III precipitation step, the Modified Fraction II+III dissolution step, and the Modified Fraction II+III suspension filtration step.

In another embodiment, the method may comprise an improvement in all of the first precipitation step, the Modified Fraction II+III precipitation step, the Modified Fraction II+III dissolution step, and the Modified Fraction II+III suspension filtration step.

In certain embodiments, one process improvement in the IgG purification methods provided herein comprises the spray addition of one or more solutions that would otherwise be introduced into a plasma fraction by fluent addition. For example, in certain embodiments the process improvement comprises the addition of alcohol (e.g., ethanol) into a plasma fraction for the purposes of precipitation of one or more protein species by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, another process improvement, which may be combined with any other process improvement, comprises the adjustment of the pH of a plasma fraction being precipitated after and/or concomitant with the addition of the precipitating agent (e.g., alcohol or polyethelene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In other embodiments, another process improvement, which may be combined with any other process improvement, comprises the use of a finely divided silica treatment step to remove impurities.

1. Preparation of Cryo-Poor Plasma

The starting material used for the preparation of concentrated IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of factor eight inhibitor bypass activity (FEIBA), Factor IX-complex, Factor VII-concentrate, or Antithrombin III-complex.

2. First Precipitation Event—Modified Fractionation I

In this step, cryo-poor plasma is typically cooled to about 0±1° C. and the pH is adjusted to between about 7.0 and about 7.5, preferably between about 7.1 and about 7.3, most preferably about 7.2. In one embodiment, the pH of the cryo-poor plasma is adjusted to a pH of at or about 7.2. Pre-cooled ethanol is then added while the plasma is stirred to a target concentration of ethanol at or about 8% v/v. At the same time the temperature is further lowered to between about −4 and about 0° C. In a preferred embodiment, the temperature is lowered to at or about −2° C., to precipitate contaminants such as $\alpha_2$-macroglobulin, $\beta_{1A}$- and $\beta_{1C}$-globulin, fibrinogen, and Factor VIII. Typically, the precipitation event will include a hold time of at least about 1 hour, although shorter or longer hold times may also be employed. Subsequently, the supernatant (Supernatant I), ideally containing the entirety of the IgG content present in the cryo-poor plasma, is then collected by centrifugation, filtration, or another suitable method.

As compared to conventional methods employed as a first fractionation step for cryo-poor plasma (Cohn et al., supra; Oncley et al., supra), the present invention provides, in several embodiments, methods that result in improved IgG yields in the Supernatant I fraction. In one embodiment, the improved IgG yield is achieved by adding the alcohol by spraying. In another embodiment, the improved IgG yield is achieved by adding a pH modifying agent by spraying. In yet another embodiment, the improved IgG yield is achieved by adjusting the pH of the solution after addition of the alcohol. In a related embodiment, the improved IgG yield is achieved by adjusting the pH of the solution during the addition of the alcohol.

In one specific aspect, the improvement relates to a method in which a reduced amount of IgG is lost in the precipitate fraction of the first precipitation step. For example, in certain embodiments, a reduced amount of IgG is lost in the precipitate fraction of the first precipitation step as compared to the amount of IgG lost in the first precipitation step of the Cohn method 6 protocol.

In certain embodiments, the process improvement is realized by adjusting the pH of the solution to between about 7.0 and about 7.5 after the addition of the precipitating alcohol. In other embodiments, the pH of the solution is adjusted to between about 7.1 and about 7.3 after addition of the precipitating alcohol. In yet other embodiments, the pH of the solution is adjusted to about 7.0 or about 7.1, 7.2, 7.3, 7.4, or 7.5 after addition of the precipitating alcohol. In a particular embodiment, the pH of the solution is adjusted to about 7.2 after addition of the precipitating alcohol. As such, in certain embodiments, a reduced amount of IgG is lost in the precipitate fraction of the first precipitation step as compared to an analogous precipitation step in which the pH of the solution is adjusted prior to but not after addition of the precipitating alcohol. In one embodiment, the pH is maintained at the desired pH during the precipitation hold or incubation time by continuously adjusting the pH of the solution. In one embodiment, the alcohol is ethanol.

In other certain embodiments, the process improvement is realized by adding the precipitating alcohol and/or the solution used to adjust the pH by spraying, rather than by fluent addition. As such, in certain embodiments, a reduced amount of IgG is lost in the precipitate fraction of the first precipitation step as compared to an analogous precipitation step in which the alcohol and/or solution used to adjust the pH is introduced by fluent addition. In one embodiment, the alcohol is ethanol.

In yet other certain embodiments, the improvement is realized by adjusting the pH of the solution to between about 7.0 and about 7.5. In a preferred embodiment, the pH of the solution is adjusted to between about 7.1 and about 7.3. In other embodiments, the pH of the solution is adjusted to at or about 7.0, 7.1, 7.2, 7.3, 7.4, or 7.5 after the addition of the precipitating alcohol and by adding the precipitating alcohol and/or the solution used to adjust the pH by spraying, rather than by fluent addition. In a particular embodiment, the pH of the solution is adjusted to at or about 7.2 after addition of the precipitating alcohol and by adding the precipitating alcohol and/or the solution used to adjust the pH by spraying, rather than by fluent addition. In one embodiment, the alcohol is ethanol.

3. Second Precipitation Event—Modified Fractionation II+III

To further enrich the IgG content and purity of the fractionation, Supernatant I is subjected to a second precipitation step, which is a modified Cohn-Oncley Fraction II+III fractionation. Generally, the pH of the solution is adjusted to a pH of between about 6.6 and about 6.8. In a preferred embodiment, the pH of the solution is adjusted to at or about 6.7. Alcohol, preferably ethanol, is then added to the solution while being stirred to a final concentration of between about 20% and about 25% (v/v) to precipitate the IgG in the fraction. In a preferred embodiment, alcohol is added to a final concentration of at or about 25% (v/v) to precipitate the IgG in the fraction. Generally, contaminants such as $\alpha_1$-lipoprotein, $\alpha_1$-antitrypsin, Gc-globulins, $\alpha_{1X}$-glycoprotin, haptoglobulin, ceruloplasmin, transferrin, hemopexin, a fraction of the Christmas factor, thyroxin binding globulin, cholinesterase, hypertensinogen, and albumin will not be precipitated by these conditions.

Prior to or concomitant with alcohol addition, the solution is further cooled to between about $-7°$ C. and about $-9°$ C. In a preferred embodiment, the solution is cooled to a temperature at or about $-7°$ C. After completion of the alcohol addition, the pH of the solution is immediately adjusted to between about 6.8 and about 7.0. In a preferred embodiment, the pH of the solution is adjusted to at or about 6.9. Typically, the precipitation event will include a hold time of at least about 10 hours, although shorter or longer hold times may also be employed. Subsequently, the precipitate (Modified Fraction II+111), which ideally contains at least about 85%, preferably at least about 90%, more preferably at least about 95%, of the IgG content present in the cryo-poor plasma, is separated from the supernatant by centrifugation, filtration, or another suitable method and collected. As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In a related embodiment, the present invention provides methods that result in a reduced loss of IgG in the Modified II+III supernatant.

As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In one embodiment, the improvement is realized by the addition of alcohol by spraying. In another embodiment, the improvement is realized by the addition of a pH modifying agent by spraying. In another embodiment, the improvement is realized by adjusting the pH of the solution after addition of the alcohol. In a related embodiment, the improvement is realized by adjusting the pH of the solution during addition of the alcohol. In another embodiment, the improvement is realized by increasing the concentration of alcohol (e.g., ethanol) to about 25% (v/v). In another embodiment, the improvement is realized by lowering the temperature of the precipitation step to between about $-7°$ C. and $-9°$ C. In a preferred embodiment, the improvement is realized by increasing the concentration of alcohol (e.g., ethanol) to about 25% (v/v) and lowering the temperature to between about $-7°$ C. and $-9°$ C. In comparison, both Cohn et al. and Oncley et al. perform precipitation at $-5°$ C. and Oncley et al. use 20% alcohol, in order to reduce the level of contaminants in the precipitate. Advantageously, the methods provided herein allow for maximal IgG yield without high levels of contamination in the final product.

Figure 8:
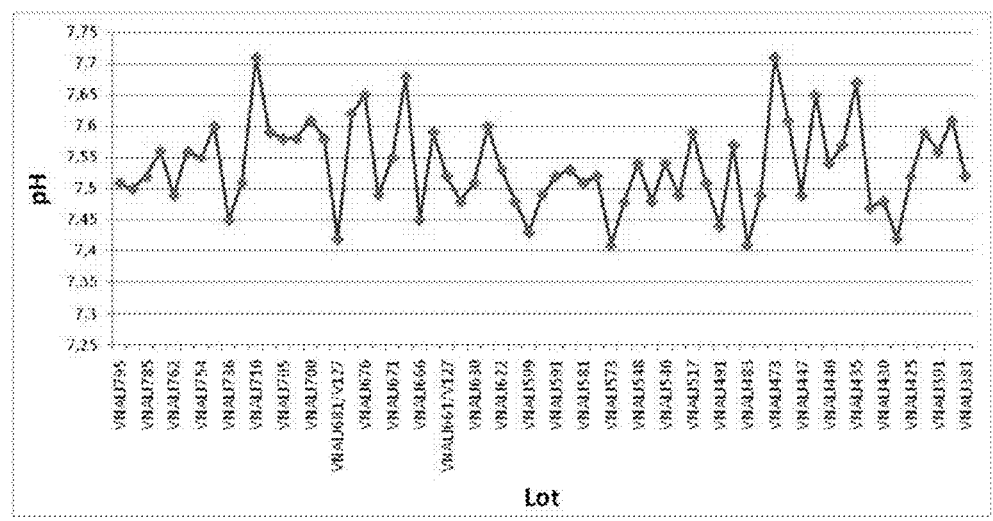
FIG. 8: Shift in pH from 6.9 of the Fraction II+III supernatant after addition of precipitating alcohol in large-scale IgG manufacturing.

It has been discovered that when the pH of the solution is adjusted to a pH of about 6.9 prior to addition of the precipitating alcohol, the pH of the solution shift from 6.9 to between about 7.4 and about 7.7, due in part to protein precipitation (see, FIG. 8). As the pH of the solution shifts away from 6.9, precipitation of IgG becomes less favorable and the precipitation of certain contaminants becomes more favorable. Advantageously, the inventors have found that by adjusting the pH of the solution after addition of the precipitating alcohol, that a higher percentage of IgG is recovered in the Fraction II+III precipitate.

Accordingly, in one aspect, the improvement relates to a method in which a reduced amount of IgG is lost in the supernatant fraction of the modified Fraction II+III precipitation step. In other words, an increased percentage of the starting IgG is present in the Fraction II+III precipitate. In certain embodiments, the process improvement is realized by adjusting the pH of the solution to between about 6.7 and about 7.1 immediately after or during the addition of the precipitating alcohol. In another embodiment, the process improvement is realized by maintaining the pH of the solution to between about 6.7 and about 7.1 continuously during the precipitation incubation period. In other embodiments, the pH of the solution is adjusted to between about 6.8 and about 7.0 immediately after or during the addition of the precipitating alcohol, or to a pH of about 6.7, 6.8, 6.9, 7.0, or 7.1 immediately after or during the addition of the precipitating alcohol. In a particular embodiment, the pH of the solution is adjusted to about 6.9 immediately after or during the addition of the precipitating alcohol. In certain embodiments, the pH of the solution is maintained at between about 6.8 to about 7.0 continuously during the precipitation incubation period, or at a pH of about 6.9 continuously during the precipitation incubation period. As such, in certain embodiments, a reduced amount of IgG is lost in the supernatant fraction of the second precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period. In one embodiment, the pH is maintained at the desired pH during the precipitation hold or incubation time by continuously adjusting the pH of the solution. In one embodiment, the alcohol is ethanol.

In another embodiment, the process improvement is realized by adding the precipitating alcohol and/or the solution used to adjust the pH by spraying, rather than by fluent addition. As such, in certain embodiments, a reduced amount of IgG is lost in the supernatant fraction of the second precipitation step as compared to an analogous precipitation step in which the alcohol and/or solution used to adjust the pH is introduced by fluent addition. In one embodiment, the alcohol is ethanol.

In another embodiment, the process improvement is realized by performing the precipitation step at a temperature between about −7° C. and about −9° C. In one embodiment, the precipitation step is performed at a temperature of at or about −7° C. In another embodiment, the precipitation step is performed at a temperature of at or about −8° C. In another embodiment, the precipitation step is performed at a temperature of at or about −9° C. In certain embodiments, the alcohol concentration of the precipitation step is between about 23% and about 27%. In a preferred embodiment, the alcohol concentration is between about 24% and about 26%. In another preferred embodiment, the alcohol concentration is at or about 25%. In other embodiments, the alcohol concentration may be at or about 23%, 24%, 25%, 26%, or 27%. In a particular embodiment, the second precipitation step is performed at a temperature of at or about −7° C. with an alcohol concentration of at or about 25%. In one embodiment, the alcohol is ethanol.

The effect of increasing the alcohol concentration of the second precipitation from 20%, as used in Oncley et al., supra, to 25% and lowering the temperature of the incubation from −5° C., as used in the Cohn and Oncley methods, to at or about −7° C. is a 5% to 6% increase in the IgG content of the modified Fraction II+III precipitate.

In another embodiment, the process improvement is realized by adjusting the pH of the solution to between about 6.7 and about 7.1, preferably at or about 6.9, immediately after or during the addition of the precipitating alcohol, maintaining the pH of the solution at a pH of between about 6.7 and about 7.1, preferably at or about 6.9, by continuously adjusting the pH during the precipitation incubation period, and by adding the precipitating alcohol and/or the solution used to adjust the pH by spraying, rather than by fluent addition. In another particular embodiment, the process improvement is realized by performing the precipitation step at a temperature between about −7° C. and about −9° C., preferably at or about −7° C. and by precipitating the IgG with an alcohol concentration of between about 23% and about 27%, preferably at or about 25%. In yet another particular embodiment, the process improvement is realized by incorporating all of the Modified Fraction II+III improvements provided above. In a preferred embodiment, the process improvement is realized by precipitating IgG at a temperature of at or about −7° C. with at or about 25% ethanol added by spraying and then adjusting the pH of the solution to at or about 6.9 after addition of the precipitating alcohol. In yet another preferred embodiment, the pH of the solution is maintained at or about 6.9 for the entirety of the precipitation incubation or hold time.

4. Extraction of the Modified Fraction II+III Precipitate

In order to solubilize the IgG content of the modified Fraction II+III precipitate, a cold extraction buffer is used to re-suspend the Fractionation II+III precipitate at a typical ratio of 1 part precipitate to 15 parts of extraction buffer. Other suitable re-suspension ratios may be used, for example from about 1:8 to about 1:30, or from about 1:10 to about 1:20, or from about 1:12 to about 1:18, or from about 1:13 to about 1:17, or from about 1:14 to about 1:16. In certain embodiments, the re-suspension ratio may be about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the modified II+III precipitate will generally have a pH between about 4.0 and about 5.5. In certain embodiments, the solution will have a pH between about 4.5 and about 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.5. In another preferred embodiment, the pH of the extraction buffer will be at or about 4.7. In another preferred embodiment, the pH of the extraction buffer will be at or about 4.9. Generally, these pH requirements can be met using a buffering agent selected from, for example, acetate, citrate, monobasic phosphate, dibasic phosphate, mixtures thereof, and the like. Suitable buffer concentrations typically range from about 5 to about 100 mM, or from about 10 to about 50 mM, or about 5, 10, 15, 20, 25, 30, 35, 40, 45, 50, 55, 60, 65, 70, 75, 80, 85, 90, 95, or 100 mM buffering agent.

The extraction buffer will preferably have a conductivity of from about 0.5 mS·cm$^{-1}$ to about 2.0 mS·cm$^{-1}$. For example, in certain embodiments, the conductivity of the extraction buffer will be about 0.5 mS·cm$^{-1}$, or about 0.6, 0.7, 0.8, 0.9, 1.0, 1.1, 1.2, 1.3, 1.4, 1.5, 1.6, 1.7, 1.8, 1.9, or about 2.0 mS·cm$^{-1}$. One of ordinary skill in the art will know how to generate extraction buffers having an appropriate conductivity.

In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

Generally, the extraction is performed at between about 0° C. and about 10° C., or between about 2° C. and about 8° C. In certain embodiments, the extraction may be performed at about 0° C., 1° C., 2° C., 3° C., 4° C., 5° C., 6° C., 7° C., 8° C., 9° C., or 10° C. In a particular embodiment, the extraction is performed at between about 2° C. and about 10° C. Typically, the extraction process will proceed for between about 60 and about 300 minutes, or for between about 120 and 240 min, or for between about 150 and 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, or about 300 minutes. In a preferred embodiment, the extraction process will proceed for at least 160 minutes with continuous stirring.

Figure 9:
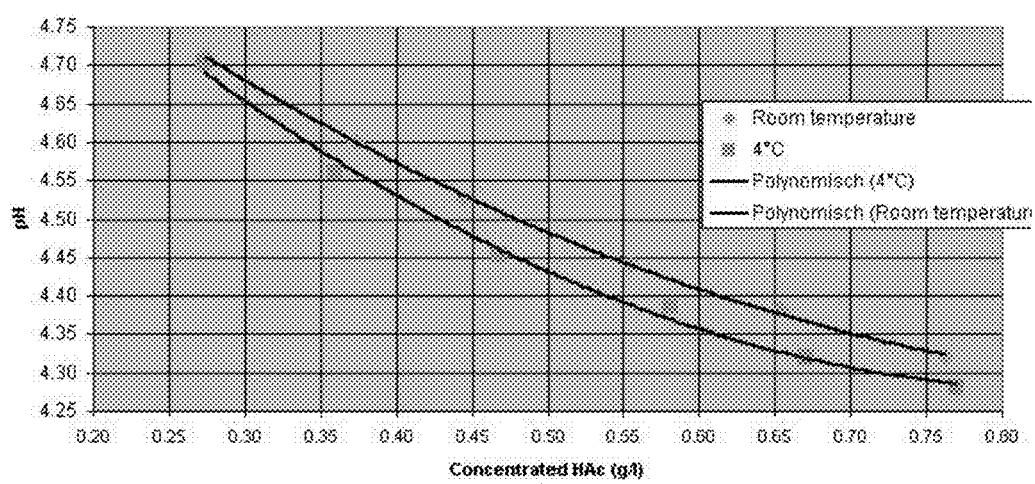
FIG. 9: Amount of glacial acetic acid versus pH in the modified Fraction II+III precipitate extraction buffer.

It has been found that employing an extraction buffer containing 5 mM monobasic sodium phosphate, 5 mM acetate, and 0.051% to 0.06% glacial acetic acid (v/v), a substantial increase in the yield increase in the final IgG composition can be obtained without jeopardizing the purity of the final product. The correlation of amount of acetic acid and extraction buffer pH is demonstrated in FIG. 9. In a preferred embodiment, the Fraction II+III precipitate is extracted with a paste to buffer ration of at or about 1:15 at a pH of at or about 4.5±0.2.

Advantageously, it has been found that compared to the current manufacturing process for GAMMAGARD® LIQUID (Baxter Healthcare), which employs an extraction buffer containing 5 mM monobasic sodium phosphate, 5 mM acetate, and 0.051% glacial acetic acid (v/v), that by increasing the glacial acetic acid content to at or about 0.06% (v/v), a substantial increase in the yield increase in the final IgG composition can be obtained. As compared to methods previously employed for the extraction of the precipitate formed by the second precipitation step (GAMMAGARD® LIQUID), the present invention provides, in several embodiments, methods that result in improved IgG yields in the Modified Fraction II+III suspension.

In one aspect, the improvement relates to a method in which a reduced amount of IgG is lost in the non-solubilized fraction of the Modified Fraction II+III precipitate. In one embodiment, the process improvement is realized by extracting the Modified Fraction II+III precipitate at a ratio of 1:15 (precipitate to buffer) with a solution containing 5 mM monobasic sodium phosphate, 5 mM acetate, and 0.06% glacial acetic acid (v/v). In another embodiment, the improvement is realized by maintaining the pH of the solution during the duration of the extraction process. In one embodiment, the pH of the solution is maintained at between about 4.1 and about 4.9 for the duration of the extraction process. In a preferred embodiment, the pH of the solution is maintained at between about 4.2 and about 4.8 for the duration of the extraction process. In a more preferred embodiment, the pH of the solution is maintained at between about 4.3 and about 4.7 for the duration of the extraction process. In another preferred embodiment, the pH of the solution is maintained at between about 4.4 and about 4.6 for the duration of the extraction process. In yet another preferred embodiment, the pH of the solution is maintained at or at about 4.5 for the duration of the extraction process.

In another aspect, the improvement relates to a method in which an increased amount of IgG is solubilized from the Fraction II+III precipitate in the Fraction II+III dissolution step. In one embodiment, the process improvement is realized by solubilizing the Fraction II+III precipitate in a dissolution buffer containing 600 mL glacial acetic acid per 1000 L. In another embodiment, the improvement relates to a method in which impurities are reduced after the IgG in the Fraction II+III precipitate is solubilized. In one embodiment, the process improvement is realized by mixing finely divided silicon dioxide ($SiO_2$) with the Fraction II+III suspension for at least about 30 minutes.

5. Pretreatment and Filtration of the Modified Fraction II+III Suspension

In order to remove the non-solubilized fraction of the Modified Fraction II+III precipitate (i.e., the Modified Fraction II+III filter cake), the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration.

Although the manufacturing process improvements described above minimize IgG losses in the initial steps of the purification process, critical impurities, including PKA activity, amidolytic activity, and fibrinogen content, are much higher when, for example, the II+III paste is extracted at pH 4.5 or 4.6, as compared to when the extraction occurs at a pH around 4.9 to 5.0 (see, Examples 2 to 5).

In order to counter act the impurities extracted in the methods provided herein, it has now been found that the purity of the IgG composition can be greatly enhanced by the addition of a pretreatment step prior to filtration/centrifugation. In one embodiment, this pretreatment step comprises addition of finely divided silica dioxide particles (e.g., fumed silica, Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, or more minutes. Generally, the treatment will be performed at between about 0° C. and about 10° C., or between about 2° C. and about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

The effect of the fumed silica treatment is exemplified by the results found in Example 17. In this example, a Fraction II+III precipitate is suspended and split into two samples, one of which is clarified with filter aid only prior to filtration (FIG. 7A) and one of which is treated with fumed silica prior to addition of the filter aid and filtration (FIG. 7B). As can be seen in the chromatographs and in the quantitated data, the filtrate sample pretreated with fumed silica had a much higher IgG purity than the sample only treated with filter aid (68.8% vs. 55.7%; compare Tables 17 and 18, respectively).

In certain embodiments, fumed silica is added at a concentration of between about 20 g/kg II+III paste and about 100 g/kg II+III paste (i.e., for a Modified Fraction II+III precipitate that is extracted at a ration of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Modified Fraction II+III suspension to a final concentration of about 40 g/16 kg II+III. Mixing takes place at about 2 to 8° C. for at least 50 to 70 minutes.

In certain embodiments, filter aid, for example Celpure C300 (Celpure) or Hyflo-Supper-Cel (World Minerals), will be added after the silica dioxide treatment, to facilitate depth filtration. Filter aid can be added at a final concentration of from about 0.1 kg/kg II+III paste to about 0.07 kg/kg II+III paste, or from about 0.2 kg/kg II+III paste to about 0.06 kg/kg II+III paste, or from about 0.3 kg/kg II+III paste to about 0.05 kg/kg II+III paste. In certain embodiments, the filter aid will be added at a final concentration of about 0.1 kg/kg II+III paste, or about 0.2, 0.3, 0.4, 0.5, 0.6, or 0.7 kg/kg II+III paste.

A significant fraction of IgG was being lost during the filtration step of the GAMMAGARD® LIQUID manufacturing process. It was found that the current methods of post-filtration wash, using 1.8 dead volumes of suspension buffer to purge the filter press frames and lines, were insufficient for maximal recovery of IgG at this step. Surprisingly, it was found that at least 3.0 dead volumes, preferably 3.6 dead volumes, of suspension buffer were required in order for efficient recovery of total IgG in the Modified Fraction II+III clarified suspension (see, Example 12 and FIG. 1). In certain embodiments, the filter press may be washed with any suitable suspension buffer. In a particular embodiment, the wash buffer will comprise, for example, 5 mM monobasic sodium phosphate, 5 mM acetate, and 0.015% glacial acetic acid (v/v).

Figure 10:
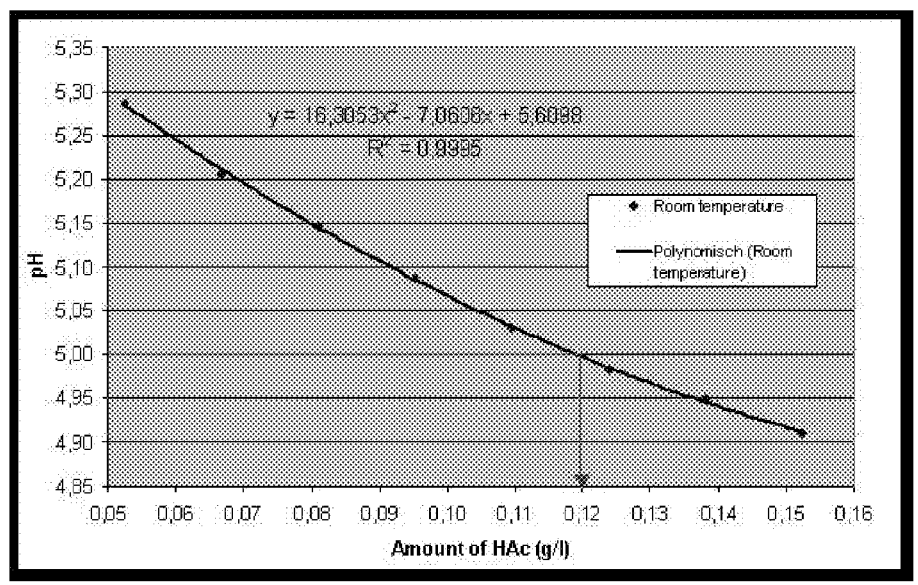
FIG. 10: Amount of glacial acetic acid versus pH in the modified Fraction II+III suspension filter post-wash buffer.

In one aspect, the improvement relates to a method in which a reduced amount of IgG is lost during the Fraction II+III suspension filtration step. In one embodiment, the process improvement is realized by post-washing the filter with at least about 3.6 dead volumes of dissolution buffer containing 150 mL glacial acetic acid per 1000 L. The relationship between the amount of glacial acetic acid and pH in the post-wash buffer is shown in FIG. 10. In one embodiment, the pH of the post-wash extraction buffer is between about 4.6 and about 5.3. In a preferred embodiment, the pH of the post-wash buffer is between about 4.7 and about 5.2. In another preferred embodiment, the pH of the post-wash buffer is between about 4.8 and about 5.1. In yet another preferred embodiment, the pH of the post-wash buffer is between about 4.9 and about 5.0.

As compared to methods previously employed for the clarification of the suspension formed from the second precipitation step (GAMMAGARD® LIQUID), the present invention provides, in several embodiments, methods that result in improved IgG yields and purity in the clarified Fraction II+III suspension. In one aspect, the improvement relates to a method in which a reduced amount of IgG is lost in the Modified Fraction II+III filter cake. In other aspect, the improvement relates to a method in which a reduced amount of an impurity is found in the clarified Fraction II+III suspension.

In one embodiment, the process improvements are realized by inclusion of a fumed silica treatment prior to filtration or centrifugal clarification of the Modified Fraction II+III suspension. In certain embodiments, the fumed silica treatment will include addition of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste, or about 0.02, 0.03, 0.04, 0.05, 0.06, or 0.07 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C. In another embodiment, the process improvements are realized by inclusion of a fumed silica treatment which reduced the levels of residual fibrinogen, amidolytic activity, and/or prekallikrein activator activity.

In another embodiment, the process improvements are realized by washing the depth filter with between about 3 and about 5 volumes of the filter dead volume after completing the Modified Fraction II+III suspension filtration step. In certain embodiments, the filter will be washed with between about 3.5 volumes and about 4.5 volumes, or at least about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 volumes of the filter dead volume. In a particular embodiment, the filter press will be washed with at least about 3.6 dead volumes of suspension buffer.

6. Detergent Treatment

In order to remove additional contaminants from the Modified Fraction II+III filtrate, the sample is next subjected to a detergent treatment. Methods for the detergent treatment of plasma derived fractions are well known in the art. Generally, any standard non-ionic detergent treatment may be used in conjunction with the methods provided herein. For example, an exemplary protocol for a detergent treatment is provided below.

Briefly, polysorbate-80 is added to the Modified Fraction II+III filtrate at a final concentration of about 0.2% (w/v) with stirring and the sample is incubated for at least 30 minutes at a temperature between about 2 to 8° C. Sodium citrate dehydrate is then mixed into the solution at a final concentration of about 8 g/L and the sample is incubated for an additional 30 minutes, with continuous of stirring at a temperature between about 2 to 8° C.

In certain embodiments, any suitable non-ionic detergent can be used. Examples of suitable non-ionic detergents include, without limitation, Octylglucoside, Digitonin, C12E8, Lubrol, Triton X-100, Nonidet P-40, Tween-20 (i.e., polysorbate-20), Tween-80 (i.e., polysorbate-80), an alkyl poly(ethylene oxide), a Brij detergent, an alkylphenol poly (ethylene oxide), a poloxamer, octyl glucoside, decyl maltoside, and the like.

In one embodiment, a process improvement is realized by adding the detergent reagents (e.g., polysorbate-80 and sodium citrate dehydrate) by spraying rather than by fluent addition. In other embodiments, the detergent reagents may be added as solids to the Modified Fraction II+III filtrate while the sample is being mixed to ensure rapid distribution of the additives. In certain embodiments, it is preferable to add solid reagents by sprinkling the solids over a delocalized surface area of the filtrate such that local overconcentration does not occur, such as in fluent addition.

7. Third Precipitation Event—Precipitation G

In order to remove several residual small proteins, such as albumin and transferrin, a third precipitation is performed at a concentration of 25% alcohol. Briefly, the pH of the detergent treated II+III filtrate is adjusted to between about 6.8 and 7.2, preferably between about 6.9 and about 7.1, most preferably about 7.0 with a suitable pH modifying solution (e.g., 1M sodium hydroxide or 1M acetic acid). Cold alcohol is then added to the solution to a final concentration of about 25% (v/v) and the mixture is incubated while stirring at between about −6° C. to about −10° C. for at least 1 hour to form a third precipitate (i.e., precipitate G). In one embodiment, the mixture is incubated for at lease 2 hours, or at least 3, 4, 5, 6, 7, 8, 9, 10, 11, 12, 13, 14, 15, 16, 17, 18, 19, 20, 21, 22, 23, 24, or more hours. In a preferred embodiment, the mixture is incubated for at least 2 hours. In a more preferred embodiment, the mixture is incubated for at least 4 hours. In an even more preferred embodiment, the mixture is incubated for at least 8 hours.

In one aspect, a process improvement relates to a method in which a reduced amount of IgG is lost in the supernatant fraction of the third precipitation step. In certain embodiments, the process improvement is realized by adjusting the pH of the solution to between about 6.8 and about 7.2 immediately after or during the addition of the precipitating alcohol. In another embodiment, the process improvement is realized by maintaining the pH of the solution to between about 6.8 and about 7.2 continuously during the precipitation incubation period. In other embodiments, the pH of the solution is adjusted to between about 6.9 and about 7.1 immediately after or during the addition of the precipitating alcohol, or to a pH of about 6.8, 6.9, 7.0, 7.1, or 7.2 immediately after or during the addition of the precipitating alcohol. In a particular embodiment, the pH of the solution is adjusted to about 7.0 immediately after or during the addition of the precipitating alcohol. In certain embodiments, the pH of the solution is maintained at between about 6.9 to about 7.1 continuously during the precipitation incubation period, or at a pH of about 7.0 continuously during the precipitation incubation period. As such, in certain embodiments, a reduced amount of IgG is lost in the supernatant fraction of the third precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period.

In one embodiment, the pH is maintained at the desired pH during the precipitation hold or incubation time by continuously adjusting the pH of the solution. In one embodiment, the alcohol is ethanol.

In another embodiment, the process improvement is realized by adding the precipitating alcohol and/or the solution used to adjust the pH by spraying, rather than by fluent addition. As such, in certain embodiments, a reduced amount of IgG is lost in the supernatant fraction of the third precipitation step as compared to an analogous precipitation step in which the alcohol and/or solution used to adjust the pH is introduced by fluent addition. In one embodiment, the alcohol is ethanol.

8. Suspension and Filtration of Precipitate G (PptG)

In order to solubilize the IgG content of the precipitate G, a cold extraction buffer is used to re-suspend the PptG. Briefly, the precipitate G is dissolved 1 to 3.5 in Water for Injection (WFI) at between about 0° C. and about 8° C. to achieve an $AU_{280-320}$ value of between about 40 to 95. The final pH of the solution, which is stirred for at least 2 hours, is then adjusted to at or about 5.2±0.2. In one embodiment, this pH adjustment is performed with 1M acetic acid. To increase the solubility of IgG, the conductivity of the suspension is increased to between about 2.5 and about 6.0 mS/cm. In one embodiment, the conductivity is increased by the addition of sodium chloride. The suspended PptG solution is then filtered with a suitable depth filter having a nominal pore size of between about 0.1 µm and about 0.4 µm in order to remove any undissolved particles. In one embodiment, the nominal pore size of the depth filter is about 0.2 µm (e.g., Cuno VR06 filter or equivalent) to obtain a clarified filtrate. In another embodiment, the suspended PptG solution is centrifuged to recover a clarified supernatant. Post-wash of the filter is performed using a sodium chloride solution with a conductivity of between about 2.5 and about 6.0 mS/cm. Typically, suitable solutions for the extraction of precipitate G include, WFI and low conductivity buffers. In one embodiment, a low conductivity buffer has a conductivity of less than about 10 mS/cm. In a preferred embodiment, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

9. Solvent Detergent Treatment

In order to inactivate various viral contaminants which may be present in plasma-derived products, the clarified PptG filtrate is next subjected to a solvent detergent (S/D) treatment. Methods for the detergent treatment of plasma derived fractions are well known in the art (for review see, Pelletier J P et al., *Best Pract Res Clin Haematol.* 2006; 19(1):205-42). Generally, any standard S/D treatment may be used in conjunction with the methods provided herein. For example, an exemplary protocol for an S/D treatment is provided below.

Briefly, Triton X-100, Tween-20, and tri(n-butyl)phosphate (TNBP) are added to the clarified PptG filtrate at final concentrations of about 1.0%, 0.3%, and 0.3%, respectively. The mixture is then stirred at a temperature between about 18° C. and about 25° C. for at least about an hour.

In one embodiment, a process improvement is realized by adding the S/D reagents (e.g., Triton X-100, Tween-20, and TNBP) by spraying rather than by fluent addition. In other embodiments, the detergent reagents may be added as solids to the clarified PptG filtrate, which is being mixed to ensure rapid distribution of the S/D components. In certain embodiments, it is preferable to add solid reagents by sprinkling the solids over a delocalized surface area of the filtrate such that local overconcentration does not occur, such as in fluent addition.

10. Ion Exchange Chromatography

In order to further purify and concentrate IgG from the S/D treated PptG filtrate, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of either a Fraction I+II+III or a Fraction II precipitate followed by a single anion exchange step performed at an alkaline pH. U.S. Pat. No. 7,553,938 describes a method involving the extraction of either a Fraction I+II+III or a Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation. The disclosures of the above publications are hereby incorporated by reference in their entireties for all purposes In one embodiment of the methods of the present invention, the S/D treated PptG filtrate may be subjected to both cation exchange chromatography and anion exchange chromatography. For example, in one embodiment, the S/D treated PptG filtrate is passed through a cation exchange column, which binds the IgG in the solution. The S/D reagents can then be washed away from the absorbed IgG, which is subsequently eluted off of the column with a high pH elution buffer having a pH between about 8.0 and 9.0. In this fashion, the cation exchange chromatography step can be used to remove the S/D reagents from the preparation, concentrate the IgG containing solution, or both. In certain embodiments, the pH elution buffer may have a pH between about 8.2 and about 8.8, or between about 8.4 and about 8.6, or a pH of about 8.0, 8.1, 8.2, 8.3, 8.4, 8.5, 8.6, 8.7, 8.8, 8.9, or 9.0. In a preferred embodiment, the pH of the elution buffer is about 8.5±0.1.

In certain embodiments, the eluate from the cation exchange column may be adjusted to a lower pH, for example between about 5.5 and about 6.5, and diluted with an appropriate buffer such that the conductivity of the solution is reduced. In certain embodiments, the pH of the cation exchange eluate may be adjusted to a pH between about 5.7 and about 6.3, or between about 5.9 and about 6.1, or a pH of about 5.5, 5.6, 5.7, 5.8, 5.9, 6.0, 6.1, 6.2, 6.3, 6.4, or 6.5. In a preferred embodiment, the pH of the eluate is adjusted to a pH of about 6.0±0.1. The eluate is then loaded onto an anion exchange column, which binds several contaminants found in the preparation. The column flow through, containing the IgG fraction, is collected during column loading and washing. In certain embodiments, the ion exchange chromatographic steps of the present invention can be performed in column mode, batch mode, or in a combination of the two.

In certain embodiments, a process improvement is realized by adding the solution used to adjust the pH by spraying, rather than by fluent addition.

11. Nanofiltration and Ultra/Diafiltration

In order to further reduce the viral load of the IgG composition provided herein, the anion exchange column effluent may be nanofiltered using a suitable nanofiltration device. In certain embodiments, the nanofiltration device will have a mean pore size of between about 15 nm and about 200 nm Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof.

Optionally, ultrafiltration/diafiltration may performed to further concentrate the nanofiltrate. In one embodiment, an open channel membrane is used with a specifically designed post-wash and formulation near the end of the production process render the resulting IgG compositions about twice as high in protein concentration (200 mg/mL) compared to state of the art IVIGs (e.g., GAMMAGARD® LIQUID) without affecting yield and storage stability. With most of the commercial available ultrafiltration membranes a concentration of 200 mg/mL IgG cannot be reached without major protein losses. These membranes will be blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not effect the virus inactivation capacity of the low pH storage step.

Subsequent to nanofiltration, the filtrate may be further concentrated by ultrafiltration/diafiltration. In one embodiment, the nanofiltrate may be concentrated by ultrafiltration to a protein concentration of between about 2% and about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example between about 0.20 M and about 0.30M, or between about 0.22M and about 0.28M, or between about 0.24M and about 0.26 mM, or at a concentration of about 2.0, 2.1, 2.2, 2.3, 2.4, 2.5, 2.6, 2.7, 2.8, 2.9, or 3.0. In a preferred embodiment, the diafiltration buffer contains at or about 0.25 M glycine.

Typically, the minimum exchange volume is at least about 3 times the original concentrate volume or at least about 4, 5, 6, 7, 8, 9, or more times the original concentrate volume. The IgG solution may be concentrated to a final protein concentration of between about 5% and about 25% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, 25% or higher. In one embodiment, a final protein concentration of at least about 23% is achieved without adding the post-wash fraction to the concentrated solution. In another embodiment, a final protein concentration of at least about 24% is achieved without adding the post-wash fraction to the concentrated solution. a final protein concentration of at least about 25% is achieved without adding the post-wash fraction to the concentrated solution. Typically, at the end of the concentration process, the pH of the solution will be between about 4.6 to 5.1.

In an exemplary embodiment, the pH of the IgG composition is adjusted to about 4.5 prior to ultrafiltration. The solution is concentrated to a protein concentration of 5±2% w/v through ultrafiltration. The UF membrane has a nominal molecular weight cut off (NMWCO) of 50,000 Daltons or less (Millipore Pellicon Polyether sulfon membrane). The concentrate is diafiltered against ten volumes of 0.25 M glycine solution, pH 4.5±0.2. Throughout the ultra-diafiltration operation the solution is maintained at a temperature of between about 2° C. to about 8° C. After diafiltration, the solution is concentrated to a protein concentration of at least 11% (w/v).

12. Formulation

Upon completion of the diafiltration step, the protein concentration of the solution is adjusted to with the diafiltration buffer to a final concentration of between about 5% and about 20% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, or 20%. In a preferred embodiment, the final protein concentration of the solution is between about 9% and about 11%, more preferably about 10%.

The formulated bulk solution is further sterilized by filtering through a membrane filter with an absolute pore size of no more than about 0.22 micron, for example about 0.2 micron. Then the solution is aseptically dispensed into final containers for proper sealing, with samples taken for testing.

In one embodiment, the IgG composition is further adjusted to a concentration of about 10.2±0.2% (w/v) with diafiltration buffer. The pH is adjusted to about 4.4 to about 4.9 if necessary. Finally, the solution is sterile filtered and incubated for three weeks at or about 30° C.

13. Alcohol Addition

Advantageously, it has been found that, for purposes of fractionating IgG from plasma, addition of alcohol by spraying rather than fluent addition results in reduced loss of IgG yields. Without being bound by theory, during fluent addition to a plasma fraction, transient local overconcentration of alcohol at the fluid ingress may lead to protein denaturation and irreversible loss and/or precipitation of IgG during steps in which IgG should remain in the supernatant. Furthermore, these effects may by amplified when large volumes of alcohol need to be added, such as in industrial scale purifications involving the fractionation of at least 100 L of pooled plasma.

The effect of alcohol addition via spraying is exemplified in Example 14, in which cryo-poor plasma samples are precipitated with 8% ethanol introduced by either fluent addition (1 and 2) or spray addition (3 and 4). As can be seen in Table 14, nearly 100% of the IgG present in the cryo-poor plasma is recovered in the supernatant when ethanol is added to the sample by spraying, while 4 to 5% of the IgG is lost upon fluent addition of alcohol. This results in an IgG loss of between about 0.20 and 0.25 g/L at this step alone. In terms of 2007 production levels, this translates into a loss of about 5.3 million grams (5,300 kilograms) of IgG. Given the current market price for IVIG, which ranges from between $50 and $100 per gram, a 4 to 5% loss at this step represents an global economic loss of up to a half billion dollars annually.

Accordingly, in one aspect of the methods provided herein, one or more precipitation steps are performed by the spray addition of alcohol. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

14. Adjustment of pH

The protein precipitation profiles of plasma fractions is highly dependent upon the pH of the solution from which the plasma proteins are being precipitated. This fact has been exploited by scientists fractionating plasma proteins since the introduction of the Cohn and Oncley methods in 1946 and 1949, respectively. Traditionally, the pH of a plasma fraction is adjusted prior to alcohol addition to facilitate the highest recovery yields for the component of interest. Advantageously, it has now been found that by adjusting the pH of the solution directly after addition of alcohol or concomitant with alcohol addition results in a more defined and reproducible precipitation. It was found that ethanol addition to plasma fractions results in fluctuations in the pH of the solution, generally by raising the pH of the solution. As such, by adjusting the pH of a plasma fraction to a predetermined pH before but not after alcohol addition, the precipitation reaction will occur at a non-optimal pH.

Likewise, precipitation of proteins from a plasma fraction will effect the electrostatic environment and will thus alter the pH of the solution. Accordingly, as a precipitation event is allowed to progress, the pH of the solution will begin to diverge from the predetermined pH value that allows for maximal recovery of the protein species of interest. This is especially true for precipitation events in which a large fraction of the protein is being precipitated, precipitation events in which a high alcohol content is used, and precipitation events that require a long incubation period.

The effect of adjusting the pH of a plasma fraction are exemplified by the results found in Example 16. In this example, IgG was precipitated from two samples of a Supernatant I fraction after spray addition of alcohol. The pH of both samples was adjusted to 6.7 before alcohol addition and readjusted to 6.9 after alcohol addition but prior to the 10 hour precipitation incubation step. In the first sample (reference), the pH was not adjusted during the 10 hour incubation, while in sample two (continuous adjustment), the pH was constantly adjusted to pH 6.9 during the 10 hour incubation. As can be seen in Table 16, after removal of the modified Fraction II+III precipitate from the samples, the first supernatant contained 0.2 g IgG/L plasma, while the second sample, in which the pH was held constant during the precipitation incubation, contained only 0.13 g IgG/L plasma. The reduced loss of 0.07 g IgG/L plasma in the second sample represents, in terms of 2007 production levels, a loss of about 1.9 million grams (1,900 kilograms) of IgG. Given the current market price for IVIG, which ranges from between $50 and $100 per gram, a 1.5% loss at this step represents an global economic loss of up to $200 million dollars annually.

Accordingly, in one aspect of the methods provided herein, the pH of a plasma fraction is adjusted directly after the addition of alcohol. In related embodiments, the pH may be adjusted before and after alcohol addition, or during and after alcohol addition, or before, during, and after alcohol addition. In a related embodiment, the pH of a solution is continuously adjusted during one or more alcohol precipitation events or incubations. In certain embodiments, the pH of a solution is continuously adjusted or maintained while the system is continuously stirred or otherwise mixed to ensure rapid and equal distribution of the pH modifying agent within the system.

Similar to the case of fluent alcohol addition, it has now been found that the fluent addition of large volumes of a pH modifying agent may cause transient local pH variations, resulting in unwanted protein denaturation or precipitation. Accordingly, in one embodiment of the methods provided herein, pH modifying agents may be introduced into one or more plasma fractionation steps by spray addition. In another embodiment of the methods provided herein, the pH of a plasma fraction or precipitation step may be adjusted by spray addition of a pH modifying agent. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

III. Concentrated IgG Compositions

IVIG compositions comprising whole antibodies have been described for the treatment of certain autoimmune conditions. (See, e.g., U.S. Patent Publication Nos. US 2002/0114802, US 2003/0099635, and US 2002/0098182.) The IVIG compositions disclosed in these references include polyclonal antibodies.

1. Aqueous IgG Compositions

In one aspect, the present invention relates to aqueous IgG compositions prepared by the methods provided herein. Generally, the IgG compositions prepared by the novel methods described herein will have high IgG content and purity. For example, IgG compositions provided herein may have a protein concentration of at least about 3% (w/v) and an IgG content of greater than about 90% purity. These high purity IgG compositions are suitable for therapeutic administration, e.g., for IVIG therapy. In one embodiment, the concentration of IgG is about 10% and is used for intravenous administration. In another embodiment, the concentration is about 20% and is used for subcutaneous or intramuscular administration.

In one embodiment, the present invention provides an aqueous IgG composition prepared by a method comprising the steps of (a) precipitating a cryo-poor plasma fraction, in a first precipitation step, with between about 6% and about 10% alcohol at a pH of between about 6.7 and about 7.3 to obtain a supernatant enriched in IgG, (b) precipitating IgG from the supernatant with between about 20% and about 30% alcohol at a pH of between about 6.7 and about 7.3 to form a first precipitate, (c) re-suspending the first precipitate formed in step (b) to form a suspension, (d) treating the suspension formed in step (c) with a detergent, (e) precipitating IgG from the suspension with between about 20% and about 30% alcohol at a pH of between about 6.7 and about 7.3 to form a second precipitate, (0 re-suspending the second precipitate formed in step (e) to form a suspension, (g) treating the suspension formed in step (f) with a solvent and/or detergent, and (h) performing at least one ion exchange chromatography fractionation thereby preparing a composition of concentrated IgG.

In a specific embodiment, an IgG composition is provided that is prepared by a method comprising the steps of (a) adjusting the pH of a cryo-poor plasma fraction to about 7.0, (b) adjusting the ethanol concentration of the cryo-poor plasma fraction of step (a) to about 25% (v/v) at a temperature between about −5° C. and about −9° C., thereby forming a mixture, (c) separating liquid and precipitate from the mixture of step (b), (d) re-suspending the precipitate of step (c) with a buffer containing phosphate and acetate, wherein the pH of the buffer is adjusted with 600 ml of glacial acetic acid per 1000 L of buffer, thereby forming a suspension, (e) mixing finely divided silicon dioxide (SiO2) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with 150 ml of glacial acetic acid per 1000 L of buffer, thereby forming a wash solution, (h) combining the filtrate of step (f) with the wash solution of step (g), thereby forming a solution, and treating the solution with a detergent, (i) adjusting the pH of the solution of step (h) to about 7.0 and adding ethanol to a final concentration of about 25%, thereby forming a precipitate, (j) separating liquid and precipitate from the mixture of step (i), (k) dissolving the precipitate in an aqueous solution comprising a solvent or detergent and maintaining the solution for at least 60 minutes, (l) passing the solution after step (k) through a cation exchange chromatography column and eluting proteins absorbed on the column in an eluate, (m) passing the eluate from step (l) through an anion exchange chromatography column to generate an effluent, (n) passing the effluent from step (m) through a nanofilter to generate a nanofiltrate, (o) passing the nanofiltrate from step (n) through an ultrafiltration membrane to generate an ultrafiltrate, and (p) diafiltrating the ultrafiltrate from step (o) against a diafiltration buffer to generate a diafiltrate having a protein concentration between about 8% (w/v) and about 12% (w/v), thereby obtaining a composition of concentrated IgG.

In certain embodiments, aqueous IgG compositions are prepared using a method provided herein that comprises improvements in two or more of the fractionation process steps described above. For example, in certain embodiments the improvements may be found in the first precipitation step, the Modified Fraction II+III precipitation step, the Modified Fraction II+III dissolution step, and/or the Modified Fraction II+III suspension filtration step.

In one embodiment, an aqueous IgG composition is provided that is prepared by a purification method described herein, wherein the method comprises the spray addition of one or more solutions that would otherwise be introduced into a plasma fraction by fluent addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, an aqueous IgG composition is provided that is prepared by a purification method described herein, wherein the method comprises adjusting the pH of a plasma fraction being precipitated after and/or concomitant with the addition of the precipitating agent (e.g., alcohol or polyethelene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In one embodiment, the present invention provides aqueous IgG compositions comprising a protein concentration of between about 30 g/L and about 250 g/L. In certain embodiments, the protein concentration of the IgG composition is between about 50 g/L and about 200 g/L, or between about 70 g/L and about 150 g/L, or between about 90 g/L and about 120 g/L, or any suitable concentration within these ranges, for example about 30 g/L, or about 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, the aqueous IgG composition will have a concentration of at or about 10%. In a particularly preferred embodiment, the composition will have a concentration of 10.2±0.2% (w/v) In another preferred embodiment, the aqueous IgG composition will have a concentration of at or about 20%.

The methods provided herein allow for the preparation of IgG compositions having very high levels of purity. In one embodiment, at least about 95% of the total protein in a composition provided herein will be IgG. In other embodiments, at least about 96% of the protein is IgG, or at least about 97%, 98%, 99%, 99.5%, or more of the total protein of the composition will be IgG. In a preferred embodiment, at least 97% of the total protein of the composition will be IgG. In another preferred embodiment, at least 98% of the total protein of the composition will be IgG. In another preferred embodiment, at least 99% of the total protein of the composition will be IgG.

Similarly, the methods provided herein allow for the preparation of IgG compositions which containing extremely low levels of contaminating agents. For example, Table 19 provides the results of impurity testing for three bulk solutions of IgG prepared by the improved methods provided herein. In certain embodiments, IgG compositions are provided that contain less than about 140 mg/L IgA. In other embodiments, the IgG composition will contain less than about 60 mg/L IgA, preferably less than about 40 mg/L IgA, most preferably less than about 30 mg/L IgA.

In another embodiment, IgG compositions are provided that contain less than about 50 mg/L IgM. In other embodiments, the IgG composition will contain less than about 25 mg/L IgM, preferably less than about 10 mg/L IgM, more preferably less than about 5 mg/L IgM, more preferably less than about 4 mg/L IgM, more preferably less than about 3 mg/L IgM, most preferably less than about 2.5 mg/L IgM.

In another embodiment, IgG compositions are provided that contain less than about 100 PL-1 nmol/mL min amidolytic activity. In other embodiments, the IgG composition will contain less than about 50 PL-1 nmol/mL min amidolytic activity, preferably less than about 25 PL-1 nmol/mL min amidolytic activity, more preferably less than about 20 PL-1 nmol/mL min amidolytic activity, more preferably less than about 15 PL-1 nmol/mL min amidolytic activity, most preferably less than about 10 PL-1 nmol/mL min amidolytic activity.

In another embodiment, IgG compositions are provided that contain less than about 20 mg/L fibrinogen. In other embodiments, the IgG composition will contain less than about 10 mg/L fibrinogen, preferably less than about 5 mg/L fibrinogen, more preferably less than about 2.5 mg/L fibrinogen, more preferably less than about 1 mg/L fibrinogen, more preferably less than about 0.5 mg/L fibrinogen, most preferably less than about 0.25 mg/L fibrinogen.

In yet another embodiment, IgG compositions are provided that consist of primarily IgG monomers/dimmers. In one embodiment, an IgG composition is provided in which at least 95%, 96%, 97%, 98%, 99%, 99.1%, 99.2%, 99.3%, 99.4%, 99.5%, 99.6%, 99.7%, 99.8%, or 99.9% of the IgG is monomeric or dimeric. In a preferred embodiment, an IgG composition is provided in which at least 97% of the IgG is monomeric or dimeric. In a more preferred embodiment, at least 99% of the IgG is monomeric or dimeric. In a more preferred embodiment, at least 99.5% of the IgG is monomeric or dimeric. In a more preferred embodiment, at least 99.7% of the IgG is monomeric or dimeric.

2. Pharmaceutical Compositions

In another aspect, the present invention provides pharmaceutical compositions and formulations comprising purified IgG prepared by the methods provided herein. Generally, the IgG pharmaceutical compositions and formulations prepared by the novel methods described herein will have high IgG content and purity. For example, IgG pharmaceutical compositions and formulations provided herein may have a protein concentration of at least about 7% (w/v) and an IgG content of greater than about 95% purity. These high purity IgG pharmaceutical compositions and formulations are suitable for therapeutic administration, e.g., for IVIG therapy. In a preferred embodiment, a pharmaceutical IgG composition is formulated for intravenous administration (e.g., IVIG therapy).

In one embodiment, the pharmaceutical compositions provided herein are prepared by formulating an aqueous IgG composition isolated using a method provided herein. Generally, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), and low pH incubation at high temperatures (Kempf et al., *Transfusion* 1991 (31)423-427 and Louie et al., *Biologicals* 1994 (22):13-19).

In certain embodiments, pharmaceutical formulations are provided having an IgG content of between about 80 g/L IgG and about 120 g/L IgG. Generally, these IVIG formulations are prepared by isolating an IgG composition from plasma using a method described herein, concentrating the composition, and formulating the concentrated composition in a solution suitable for intravenous administration. The IgG compositions may be concentrated using any suitable method known to one of skill in the art. In one embodiment, the composition is concentrated by ultrafiltration/diafiltration. In some embodiments, the ultrafiltration device used to concentrate the composition will employ an ultrafiltration membrane having a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa. Buffer exchange may be achieved using any suitable technique known to one of skill in the art. In a specific embodiment, buffer exchange is achieved by diafiltration.

In one specific embodiment, a pharmaceutical composition of IgG is provided, wherein the IgG composition was purified from plasma using a method comprising the steps of (a) precipitating a cryo-poor plasma fraction, in a first precipitation step, with between about 6% and about 10% alcohol at a pH of between about 6.7 and about 7.3 to obtain a supernatant enriched in IgG, (b) precipitating IgG from the supernatant with between about 20% and about 30% alcohol at a pH of between about 6.7 and about 7.3 to form a first precipitate, (c) re-suspending the first precipitate formed in step (b) to form a suspension, (d) treating the suspension formed in step (c) with a detergent, (e) precipitating IgG from the suspension with between about 20% and about 30% alcohol at a pH of between about 6.7 and about 7.3 to form a second precipitate, (0 re-suspending the second precipitate formed in step (e) to form a suspension, (g) treating the suspension formed in step (f) with a solvent and/or detergent, (h) performing at least one ion exchange chromatography fractionation; (i) performing a solvent detergent treatment; and (j) subjecting the composition to nanofiltration, thereby preparing a composition of IgG.

In a specific embodiment, a pharmaceutical composition of IgG is provided, wherein the IgG composition was purified from plasma using a method comprising the steps of (a) adjusting the pH of a cryo-poor plasma fraction to about 7.0, (b) adjusting the ethanol concentration of the cryo-poor plasma fraction of step (a) to about 25% (v/v) at a temperature between about −5° C. and about −9° C., thereby forming a mixture, (c) separating liquid and precipitate from the mixture of step (b), (d) re-suspending the precipitate of step (c) with a buffer containing phosphate and acetate, wherein the pH of the buffer is adjusted with 600 ml of glacial acetic acid per 1000 L of buffer, thereby forming a suspension, (e) mixing finely divided silicon dioxide (SiO2) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with 150 ml of glacial acetic acid per 1000 L of buffer, thereby forming a wash solution, (h) combining the filtrate of step (f) with the wash solution of step (g), thereby forming a solution, and treating the solution with a detergent, (i) adjusting the pH of the solution of step (h) to about 7.0 and adding ethanol to a final concentration of about 25%, thereby forming a precipitate, (j) separating liquid and precipitate from the mixture of step (i), (k) dissolving the precipitate in an aqueous solution comprising a solvent or detergent and maintaining the solution for at least 60 minutes, (l) passing the solution after step (k) through a cation exchange chromatography column and eluting proteins absorbed on the column in an eluate, (m) passing the eluate from step (l) through an anion exchange chromatography column to generate an effluent, (n) passing the effluent from step (m) through a nanofilter to generate a nanofiltrate, (o) passing the nanofiltrate from step (n) through an ultrafiltration membrane to generate an ultrafiltrate, and (p) diafiltrating the ultrafiltrate from step (o) against a diafiltration buffer to generate a diafiltrate having a protein concentration between about 8% (w/v) and about 12% (w/v), thereby obtaining a composition of concentrated IgG.

In certain embodiments, a pharmaceutical composition of IgG is provided, wherein the IgG composition is prepared using a method provided herein that comprises improvements in two or more of the fractionation process steps described above. For example, in certain embodiments the improvements may be found in the first precipitation step, the Modified Fraction II+III precipitation step, the Modified Fraction II+III dissolution step, and/or the Modified Fraction II+III suspension filtration step.

In certain embodiments, a pharmaceutical composition of IgG is provided, wherein the IgG composition is prepared using a purification method described herein, wherein the method comprises the spray addition of one or more solutions that would otherwise be introduced into a plasma fraction by fluent addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, a pharmaceutical composition of IgG is provided, wherein the IgG composition is prepared by a purification method described herein, wherein the method comprises adjusting the pH of a plasma fraction being precipitated after and/or concomitant with the addition of the precipitating agent (e.g., alcohol or polyethelene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In one embodiment, the present invention provides a pharmaceutical composition of IgG comprising a protein concentration of between about 70 g/L and about 130 g/L. In certain embodiments, the protein concentration of the IgG composition is between about 80 g/L and about 120 g/L, preferably between about 90 g/L and about 110 g/L, most preferably of about 100 g/L, or any suitable concentration within these ranges, for example about 70 g/L, 75 g/L, 80 g/L, 85 g/L, 90 g/L, 95 g/L, 100 g/L, 105 g/L, 110 g/L, 115 g/L, 120 g/L, 125 g/L, or 130 g/L. In a preferred embodiment, a pharmaceutical composition is provided having a protein concentration of at or about 100 g/L. In a particularly preferred embodiment, the pharmaceutical composition will have a protein concentration of at or about 102 g/L.

In another embodiment, the present invention provides a pharmaceutical composition of IgG comprising a protein concentration of between about 170 g/L and about 230 g/L. In certain embodiments, the protein concentration of the IgG composition is between about 180 g/L and about 220 g/L, preferably between about 190 g/L and about 210 g/L, most preferably of about 200 g/L, or any suitable concentration within these ranges, for example about 170 g/L, 175 g/L, 180 g/L, 185 g/L, 190 g/L, 195 g/L, 200 g/L, 205 g/L, 210 g/L, 215 g/L, 220 g/L, 225 g/L, or 230 g/L. In a preferred embodiment, a pharmaceutical composition is provided having a protein concentration of at or about 200 g/L.

The methods provided herein allow for the preparation of IgG pharmaceutical compositions having very high levels of purity. For example, in one embodiment, at least about 95% of the total protein in a composition provided herein will be IgG. In other embodiments, at least about 96% of the protein is IgG, or at least about 97%, 98%, 99%, 99.5%, or more of the total protein of the composition will be IgG. In a preferred embodiment, at least 97% of the total protein of the composition will be IgG. In another preferred embodiment, at least 98% of the total protein of the composition will be IgG. In another preferred embodiment, at least 99% of the total protein of the composition will be IgG.

Similarly, the methods provided herein allow for the preparation of IgG pharmaceutical compositions which containing extremely low levels of contaminating agents. For example, in certain embodiments, IgG compositions are provided that contain less than about 100 mg/L IgA. In other embodiments, the IgG composition will contain less than about 50 mg/L IgA, preferably less than about 35 mg/L IgA, most preferably less than about 20 mg/L IgA.

The pharmaceutical compositions provided herein will typically comprise one or more buffering agents or pH stabilizing agents suitable for intravenous, subcutaneous, and/or intramuscular administration. Non-limiting examples of buffering agents suitable for formulating an IgG composition provided herein include glycine, citrate, phosphate, acetate, glutamate, tartrate, benzoate, lactate, histidine or other amino acids, gluconate, malate, succinate, formate, propionate, carbonate, or any combination thereof adjusted to an appropriate pH. Generally, the buffering agent will be sufficient to maintain a suitable pH in the formulation for an extended period of time. In a preferred embodiment, the buffering agent is glycine.

In some embodiments, the concentration of buffering agent in the formulation will be between about 100 mM and about 400 mM, preferably between about 150 mM and about 350 mM, more preferably between about 200 mM and about 300 mM, most preferably about 250 mM. In a particularly preferred embodiment, the IVIG composition will comprise between about 200 mM and about 300 mM glycine, most preferably about 250 mM glycine.

In certain embodiments, the pH of the formulation will be between about 4.1 and about 5.6, preferably between about 4.4 and about 5.3, most preferably between about 4.6 and about 5.1. In particular embodiments, the pH of the formulation may be about 4.1, 4.2, 4.3, 4.4, 4.5, 4.6, 4.7, 4.8, 4.9, 5.0, 5.1, 5.2, 5.3, 5.4, 5.5, or 5.6. In a preferred embodiment, the pH of the formulation will be between about 4.6 and about 5.1.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

Typically, the formulations provided herein will have osmolarities that are comparable to physiologic osmolarity, about 285 to 295 mOsmol/kg (Lacy et al., *Drug Information Handbook—Lexi-Comp* 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg.

The IgG formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, or 24 months at room temperature. The formulation will also generally be stable 6 or at least about 18 months under refrigerated conditions (typically between about 2° C. and about 8° C.), or for at least about 21, 24, 27, 30, 33, 36, 39, 42, or 45 months under refrigerated conditions.

IV. Methods of Treatment

As routinely practiced in the modern medicine, sterilized preparations of concentrated immunoglobulins (especially IgGs) are used for treating medical conditions that fall into these three main classes: immune deficiencies, inflammatory and autoimmune diseases, and acute infections. These IgG preparations may also be useful for treating multiple sclerosis (especially relapsing-remitting multiple sclerosis or RRMS), Alzheimer's disease, and Parkinson's disease. The purified IgG preparation of this invention is suitable for these purposes, as well as other clinically accepted uses of IgG preparations.

The FDA has approved the use of IVIG to treat various indications, including allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), and kidney transplant with a high antibody recipient or with an ABO incompatible donor. In certain embodiments, the IVIG compositions provided herein are useful for the treatment or management of these diseases and conditions.

Furthermore, off-label uses for IVIG are commonly provided to patients for the treatment or management of various indications, for example, chronic fatigue syndrome, *clostridium difficile* colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, and hypogammaglobulinemia. In certain embodiments, the IVIG compositions provided herein are useful for the treatment or management of these diseases and conditions.

Finally, experimental use of IVIG for the treatment or management of diseases including primary immune deficiency, RRMS, Alzheimer's disease, and Parkinson's disease has been proposed (U.S. Patent Application Publication No. U.S. 2009/0148463, which is herein incorporated by reference in its entirety for all purposes). In certain embodiments, the IVIG compositions provided herein are useful for the treatment or management of primary immune deficiency, RRMS, Alzheimer's disease, or Parkinson's disease. In certain embodiments comprising daily administration, an effective amount to be administered to the subject can be determined by a physician with consideration of individual differences in age, weight, disease severity, route of administration (e.g., intravenous v. subcutaneous) and response to the therapy. In certain embodiments, an immunoglobulin preparation of this invention can be administered to a subject at about 5 mg/kilogram to about 2000 mg/kilogram each day. In additional embodiments, the immunoglobulin preparation can be administered in amounts of at least about 10 mg/kilogram, at last 15 mg/kilogram, at least 20 mg/kilogram, at least 25 mg/kilogram, at least 30 mg/kilogram, or at least 50 mg/kilogram. In additional embodiments, the immunoglobulin preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin preparation can be greater or less. Further, the immunoglobulin preparations can be administered in one or more doses per day. Clinicians familiar with the diseases treated by IgG preparations can determine the appropriate dose for a patient according to criteria known in the art.

In accordance with the present invention, the time needed to complete a course of the treatment can be determined by a physician and may range from as short as one day to more than a month. In certain embodiments, a course of treatment can be from 1 to 6 months.

An effective amount of an IVIG preparation is administered to the subject by intravenous means. The term "effective amount" refers to an amount of an IVIG preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an IVIG preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg.

The dosage and frequency of IVIG treatment will depend upon, among other factors. the disease or condition being treated and the severity of the disease or condition in the patient. Generally, for primary immune dysfunction a dose of between about 100 mg/kg and about 400 mg/kg body weight will be administered about every 3 to 4 weeks. For neurological and autoimmune diseases, up to 2 g/kg body weight is implemented for three to six months over a five day course once a month. This is generally supplemented with maintenance therapy comprising the administration of between about 100 mg/kg and about 400 mg/kg body weight about once every 3 to 4 weeks. Generally, a patient will receive a dose or treatment about once every 14 to 35 days, or about every 21 to 28 days. The frequency of treatment will depend upon, among other factors. the disease or condition being treated and the severity of the disease or condition in the patient.

In a preferred embodiment, a method of treating an immunodeficiency, autoimmune disease, or acute infection in a human in need thereof is provided, the method comprising administering a pharmaceutical IVIG composition of the present invention. In a related embodiment, the present invention provides IVIG compositions manufactured according to a method provided herein for the treatment of an immunodeficiency, autoimmune disease, or acute infection in a human in need thereof.

In certain embodiments, the immunodeficiency, autoimmune disease, or acute infection is selected from allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), kidney transplant with a high antibody recipient or with an ABO incompatible donor, chronic fatigue syndrome, *clostridium difficile* colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, hypogammaglobulinemia, primary immune deficiency, RRMS, Alzheimer's disease, and Parkinson's disease.

EXAMPLES

The following examples are provided by way of illustration only and not by way of limitation. Those of skill in the art will readily recognize a variety of non-critical parameters that could be changed or modified to yield essentially the same or similar results.

Example 1

The present example demonstrates that significant amounts of fibrinogen, amidolytic activity, prekallikrein activity, and lipoproteins can be removed from an extracted modified Fraction II+III paste suspension by treatment with Aerosil prior to filtration.

Fumed silica (Aerosil 380) is currently used to adsorb fibrinogen, amidolytic activity, prekallikrein activity, and lipoproteins. To investigate the effect of Aerosil in more detail, six modified Fraction II+III suspensions were treated with varying amounts of Aerosil prior to filtration Briefly, dissolution buffer containing 5 mM sodium acetate/5 mM sodium dihydrogen phosphate buffer pH 4.5 was used to re-suspend modified II+III paste, prepared as described herein, at a ratio of 15 grams dissolution buffer per gram II+III paste. After paste addition, the suspension was stirred for one hour at between 2° C. and 8° C. in a pH controlled environment (pH IPC limits: 4.9 to 5.3). We have found that the pH of this suspension normally shifts to a pH of about 5.1, and thus further pH adjustment is not necessary. After an additional extraction, for at least 120 minutes, Aerosil 380, at between 0 and 100 mg per gram II+III paste, was added to the containers and the suspensions were incubated for one hour. Diatomaceous earth was added prior to depth filtration with a Cuno 50SA filter. After filtration, the filters were washed with extraction buffer containing 8 g $L^{-1}$ citrate and 0.2% polysorbate 80 (pH 5.0) and the wash was added to the filtrate. The combined filtrate and wash solution was then treated with Polysorbate 80 to further solubilize hydrophobic impurities, for example lipoproteins, and the IgG was precipitated with 25% ethanol (pH 7) at between −8° C. and −10° C. The resulting Ppt G precipitate was almost white and possessed higher IgG purity. The precipitate was then dissolved in purified water at a ratio of 7 grams water per 2 grams Ppt G precipitate.

The IgG solutions were analyzed for IgG recovery and impurities following the Cuno filtration step. Specifically, levels of amidolytic activity (PL-1), PKA activity, and fibrinogen were measured (Table 3). Notably, as seen in Table 3, extraction protocols using 40 to 60 mg Aerosil 380 per g II+III paste resulted in acceptable levels of IgG recovery with significant decreases in amidolytic and PKA activity, as well as a significant decrease in the level of fibrinogen in the filtrate. Compared to extractions performed without Aerosil treatment, the addition of 40 mg Aerosil 380 per gram II+III paste resulted in an almost 90% reduction of PKA activity and fibrinogen content and a 60% reduction of amidolytic activity, while maintaining similar IgG recovery (73%).

TABLE 1

Effect of the amount of Aerosil 380 at the II + III Cuno Filtration step (Extraction with GAMMAGARD ® LIQUID Conditions)

| Aerosil mg $g^{-1}$ II + III paste | IgG g $L^{-1}$ plasma | IgG Recovery | PL-1 µmol $min^{-1}$ $g^{-1}$ protein (Ppt G) | PKA IU $g^{-1}$ protein (Ppt G) | Fibrinogen mg $g^{-1}$ protein (Ppt G) |
|---|---|---|---|---|---|
| 0 | 4.9 | 72% | 1.3 | 2403 | 19.5 |
| 20 | 5.2 | 82% | 0.7 | 974 | 8.2 |
| 40 | 4.8 | 73% | 0.5 | 290 | 2.1 |
| 60 | 4.8 | 71% | 0.3 | 90 | 0.1 |
| 80 | 4.2 | 63% | below detection limit | 37 | 0.0 |
| 100 | 4.3 | 65% | below detection limit | 16 | 0.0 |

Example 2

The present example demonstrates that significant amounts of fibrinogen can be removed from an extracted modified Fraction II+III paste suspension by treatment with Aerosil prior to filtration. One purpose of the present experiment was to find suitable conditions for efficient fibrinogen removal without incurring significant losses of IgG.

Modified II+III paste, prepared according to the method provided herein, was dissolved in 5 mM sodium acetate/5 mM monobasic sodium phosphate buffer pH 4.5. The dissolution ratio was 15 kg of buffer per 1 kg II+III paste. The amount of acetic acid added to the buffer was chosen in a way that pH after sixty minutes stirring was 4.9. In order to fully homogenize the suspension, it was stirred up to twenty hours at 2 to 8° C. before being separated into 6 portions of 50 ml each in 100 ml beakers, where varying amounts of Aerosil 380 were already present, as given in Table 2. The II+III suspension solutions were then stirred for 80 minutes in the presence of the Aerosil, prior to processing and analysis. After stirring all samples were centrifuged with a Heraeus Cryofuge 8500i at 4600 RPM for 30 minutes at 4° C. in 50 ml falcon tubes.

In this experiment, IgG measurements were taken using the nephelometric test, which was chosen due to the more accurate values, compared to the ELISA test, at the high concentrations found in II+III suspension solutions. To minimize the irritation of unspecific turbidity, the samples were filtered through 0.45 µm filters prior to testing. For IgM, IgA, and fibrinogen, ELISA tests were preferred due to the lower concentrations of these impurities in the suspension. The results of the experiment are shown below in Table 2.

To further characterize the effect of Aerosil treatment on fibrinogen removal and IgG loss as described in Example 1, Aerosil concentrations were further titrated between 0 mg and 40 mg per gram modified II+III paste. The results shown in Table 2 confirm the high capacity of Aerosil to reduce fibrinogen in this fraction. Notably, use of 40 mg per gram II+III paste results in almost 90% reduction of fibrinogen, while only reducing IgG recovery in the filter cake by 10%.

TABLE 2

Results from the variation of dissolution conditions after extraction of II + III with 5 mM NaAc/5 mM NaH$_2$PO$_4$ pH 4.5 at a dissolution ratio of 1 kg II + III plus 15 kg of buffer after centrifugation

| Dissolution conditions | | | | | Values in supernatant | | | | | | | | | | |
|---|---|---|---|---|---|---|---|---|---|---|---|---|---|---|---|
| | additional stirring time (min) | pH | conductivity (mS cm$^{-1}$) | Protein (Biuret) | | IgM ELISA | | IgG neph. | | IgA ELISA | | Fibrinogen ELISA | | | |
| Conditions | | | | (gL$^{-1}$) | (g) | (gL$^{-1}$ plasma) | µg mL$^{-1}$ | (gL$^{-1}$ plasma) | Mg mL$^{-1}$ | (gL$^{-1}$ plasma) | µg mL$^{-1}$ | (gL$^{-1}$ plasma) | µg mL$^{-1}$ | (gL$^{-1}$ plasma) | |
| Blank 80 min | mg · g$^{-1}$ II + III paste | 80 | 5.0 | 1.5 | 13.76 | 0.69 | 8.5 | 476 | 0.29 | 7.19 | 4.44 | 993 | 0.61 | 400 | 0.25 |
| Aerosil 5 | | 80 | 5.0 | 1.5 | 13.40 | 0.67 | 8.3 | 457 | 0.28 | 7.30 | 4.51 | 983 | 0.61 | 353 | 0.22 |
| Aerosil 10 | | 80 | 5.0 | 1.5 | 13.44 | 0.67 | 8.3 | 464 | 0.29 | 6.97 | 4.30 | 1009 | 0.62 | 272 | 0.17 |
| Aerosil 15 | | 80 | 5.0 | 1.5 | 12.01 | 0.60 | 7.4 | 451 | 0.28 | 7.04 | 4.35 | 1005 | 0.62 | 230 | 0.14 |
| Aerosil 30 | | 80 | 5.0 | 1.5 | 12.49 | 0.62 | 7.7 | 468 | 0.29 | 6.77 | 4.18 | 944 | 0.58 | 95 | 0.06 |
| Aerosil 40 | | 80 | 5.0 | 1.5 | 12.21 | 0.61 | 7.5 | 449 | 0.28 | 6.71 | 4.14 | 899 | 0.56 | 41 | 0.03 |

Example 3

The present example demonstrates suitable conditions that allow for highly efficient extraction of IgG from a modified Fraction II+III paste, while limiting the levels of detrimental impurities. Specifically, parameters including the concentration of acetic acid used in the II+III dissolution buffer and aerosil treatment of the extracted solution prior to filtration were examined.

II+III paste was extracted in 5 mM sodium acetate, 5 mM sodium dihydrogen phosphate and variable amounts of concentrated acetic acid, as shown in Table 1, for 180 minutes at between 2° C. and 8° C., followed by addition of Aerosil 380 as shown in Table 1. After one hour of stirring, the suspension was clarified by Cuno 50SA filtration in the presence of diatomaceous earth. Post-wash of the filter was carried out with the same buffer as for the extraction except the different amount of acetic acid, as given in Table 1, using 40% of the volume of the suspension prior to filtration. Precipitate G precipitation in the presence of 25% ethyl alcohol; 8 g L$^{-1}$ sodium citrate, and 0.2% Tween 80 (pH 7) at −8° C. was performed and after 8 hours hold time, separation was performed by centrifugation with Heraeus Cryofuge 8500i in stainless steel beakers at 4600 RPM for 30 minutes at −10° C. The precipitate was dissolved in a 1:2 ratio in purified water.

TABLE 3

Table 3. The influence of the acetic acid amount of pH adjustment of extraction buffer and Aerosil amount for clarification on IgG yield and purity in Ppt G and IgG loss in the filter cake

| | | Aerosil (mg g$^{-1}$ II + III) | | | |
|---|---|---|---|---|---|
| | | 0 | 20 | 40 | 40 |
| dissolution buffer | acetic acid (g L$^{-1}$) | 0.40 | 0.40 | 0.40 | 0.51 |
| | pH | 4.52 | 4.52 | 4.52 | 4.46 |
| II + III extract | pH | 5.00 | 5.00 | 5.00 | 4.94 |
| | conductivity (mS cm$^{-1}$) | 1.340 | 1.340 | 1.340 | 1.344 |
| pre/post-wash buffer | acetic acid (g L$^{-1}$) | 0.12 | 0.12 | 0.12 | 0.12 |
| | pH | 5.02 | 5.02 | 5.02 | 5.02 |

TABLE 3-continued

Table 3. The influence of the acetic acid amount of pH adjustment of extraction buffer and Aerosil amount for clarification on IgG yield and purity in Ppt G and IgG loss in the filter cake

| | | Aerosil (mg g$^{-1}$ II + III) | | | |
|---|---|---|---|---|---|
| | | 0 | 20 | 40 | 40 |
| filtrate II + III | CAE albumin (%) | 11.9 | 12.5 | 12.3 | 10.7 |
| | CAE α/β-globulin | 25.5 | 22.9 | 18.9 | 17.2 |
| | CAE denatured protein | 3.2 | 0.0 | 0.0 | 0.0 |
| | CAE (% γ-globulin) | 59.4 | 64.6 | 68.8 | 72.1 |
| | pH | 5.00 | 5.03 | 5.04 | 4.92 |
| IgG loss filter cake | (g L$^{-1}$ plasma) | 0.09 | 0.20 | 0.56 | 0.29 |
| PptG dissolved | CAE albumin (%) | 0.3 | 0.5 | 0.3 | 0.3 |
| | CAE α/β-globulin | 16.2 | 14.3 | 12.5 | 13.0 |
| | CAE denatured protein | 0.0 | 0.0 | 0.0 | 0.0 |
| | CAE (% γ-globulin) | 83.5 | 85.2 | 87.2 | 86.7 |
| | fibrogen (mg L$^{-1}$ plasma) | 129 | 32 | <4 | 4 |
| | PKA (IU mg$^{-1}$ protein) | 126 | 60 | 9 | 10 |
| | PL-1 (µmol mL$^{-1}$ g$^{-1}$) | 0.9 | 0.6 | 0.5 | 0.6 |

TABLE 3-continued

Table 3. The influence of the acetic acid amount of pH adjustment of extraction buffer and Aerosil amount for clarification on IgG yield and purity in Ppt G and IgG loss in the filter cake

| | | Aerosil (mg g$^{-1}$ II + III) | | | |
|---|---|---|---|---|---|
| | | 0 | 20 | 40 | 40 |
| PptG supernatant | pH | 7.20 | 7.35 | 7.30 | 6.96 |
| IgG loss supernatant PptG | (g L$^{-1}$ plasma) | 0.14 | 0.13 | 0.11 | 0.09 |

As can be seen in Table 1, Aerosil addition to the II+III paste suspension has a marked influence on γ-globulin purity in the Ppt G fraction. Without Aerosil the γ-globulin purity is only 83.5%, while addition of 40 mg Aerosil per gram II+III paste to the II+III paste suspension increases the γ-globulin purity to 87.2%. As evidenced, Aerosil treatment leads to a significant reduction of fibrinogen, PKA and amidolytic activity. One drawback of the impurity adsorption on Aerosil is that IgG loss in the filter cake is increased with increasing amounts of Aerosil. However, as shown in Table 1, higher concentrations of acetic acid in the extraction buffer partially counterbalances the effect of Aerosil on IgG loss in the filter cake, and further reduced IgG loss in the supernatant Ppt G fraction. As can be seen in Table 1, increasing the amount of acetic acid in the dissolution buffer from 400 μL per L paste to 510 μL per L paste, reduced the amount of IgG lost in the filter cake by almost 50%. Advantageously, the higher acetic acid concentration does not affect the γ-globulin purity in the Ppt G fraction (87.2% pure using 400 μL per L paste vs. 86.7% pure using 510 μL per L paste). Furthermore, the results show that the difference in pH value caused by the different amount of acetic acid is negligible, due to the high buffer capacity of acetic acid near its pka value of 4.75 (Merck). This suggests that for better accuracy in large-scale manufacturing, acetic acid should be added by weight. Thus, the influence of Aerosil on purity is much higher than the influence of acetic acid on purity, in the investigated range, as shown with the γ-globulin content measured by CAE.

Example 4

The results found in Example 3 suggested that the amount of IgG lost in the filter cake is strongly dependent on the amount of acetic acid used for pH adjustment of the extraction buffer at a given Aerosil concentration. In order to further characterize this effect, modified II+III paste was extracted in purified water for about 120 minutes to obtain a homogeneous suspension and divided into 4 parts. These parts were adjusted to pH 3.8, 4.2, 4.6, and 5.0, respectively, with 1M acetic acid followed by a second extraction time for another 120 minutes. Afterwards, Aerosil treatment was done with 40 mg Aerosil 380 per gram II+III paste. After one hour stirring the suspension was clarified by Cuno 50SA filtration in the presence of diatomaceous earth. Post-wash of the filter was carried out with 100 percent of the volume of the suspension prior filtration with extraction buffer adjusted to the pH as given above. The filtrate was treated with 8 g L$^{-1}$ sodium citrate and 0.2% Tween 80, adjusted to pH 7.0, and IgG was precipitated with 25% alcohol at −8° C. PptG precipitate was recovered by centrifugation at 4600 RPM for 30 minutes at −10° C. in a Heraeus Cryofuge 8500i using stainless steel beakers. The precipitate was then dissolved in purified water at a ratio of 7 grams water per 2 grams Ppt G precipitate. The relevant fractions were then assayed for IgG recovery, PKA activity, fibrinogen content, and amidolytic activity, to determine the pH dependence of recovery (Table 4).

TABLE 4 pH dependent removal of fibrinogen, PKA and amidolytic activity by extraction and clarification with Aerosil treatment

| pH extraction and clarification acetic acid | concentration of acetic acid after pH adjustment (mM) | IgG loss in filter cake (g L$^{-1}$ plasma) | IgG loss in PptG supernatant (g L$^{-1}$ plasma) | IgG loss Σ (g L$^{-1}$ plasma) | Precipitate G | | |
|---|---|---|---|---|---|---|---|
| | | | | | PKA (IU mg$^{-1}$) | fibrinogen (mg L$^{-1}$ plasma) | PL-1 (μmol mL$^{-1}$ g$^{-1}$) |
| 3.8 | 75 | 0.02 | 0.85 | 0.87 | 138 | 243 | — |
| 4.2 | 25 | 0.04 | 0.53 | 0.57 | 35 | 182 | — |
| 4.6 | 10 | 0.07 | 0.05 | 0.12 | 2 | 99 | 2 |
| 5.0 | 5 | 0.19 | 0.06 | 0.25 | 0.6 | 3 | 0.5 |
| 3.8 | 75 | — | — | — | 116 | 304 | 3.8 |
| 4.2 | 25 | 0.02 | 0.34 | 0.36 | 44 | 313 | 2.6 |
| 4.6 | 10 | 0.04 | 0.52 | 0.56 | 8 | 148 | 1.7 |
| 5.0 | 5 | 0.14 | 0.09 | 0.23 | 3 | 10 | <0.2 |

Table 4 shows that PKA, amidolytic activity (PL-1), and fibrinogen removal with Aerosil is less effective at lower pH during clarification. It can be seen from the results obtained here, that the most effective pH for effective removal of PKA, amidolytic activity (PL-1), and fibrinogen, while maintaining efficient IgG recovery in the Ppt G fraction, is about pH 5. High concentrations of acetic acid lead to a significant IgG loss in Ppt G supernatant (0.85 g L$^{-1}$ in the presence of 75 mM acetic acid) while IgG loss in the filter cake is minimized.

Example 5

To determine the dependence of Aerosil treatment on the results found in Example 4, the experiment was repeated, but with the Aerosil treatment step omitted. Briefly, II+III paste was extracted in purified water for about 120 minutes to obtain a homogeneous suspension and divided into 4 parts. These parts were adjusted to pH 3.8, 4.2, 4.6, and 5.0, respectively, with 1M acetic acid followed by a second extraction time for another 120 minutes. Afterwards, the suspension was clarified by Cuno 50SA filtration in the presence of diatomaceous earth. Post-wash of the filter was carried out with 100 percent of the volume of the suspension prior filtration with extraction buffer adjusted to the pH as given above. The filtrate was treated with 8 g L$^{-1}$ sodium citrate and 0.2%

Tween 80, adjusted to pH 7.0, and IgG was precipitated with 25% alcohol at −8° C. Ppt G precipitate was recovered by centrifugation at 4600 RPM for 30 minutes at −10° C. in a Heraeus Cryofuge 8500i using stainless steel beakers. The precipitate was then dissolved in purified water at a ratio of 7 grams water per 2 grams Ppt G precipitate. The relevant fractions were then assayed for IgG recovery, PKA activity, fibrinogen content, and amidolytic activity, to determine the pH dependence of recovery (Table 5).

II+III paste is extracted at a pH of around 4.5 to 4.6. However, it is also evidenced in the previous examples, that critical impurities, including PKA activity, amidolytic activity, and fibrinogen content, are much higher when the II+III paste is extracted at pH 4.5 or 4.6 compared to when the extraction occurs at a pH around 4.9 to 5.0. Accordingly, the present example was performed to determine if the higher impurity levels seen when the II+III paste is extracted at pH 4.5 could be offset by increasing the amount of Aerosil used to adsorb

TABLE 5 pH dependent removal of fibrinogen, PKA and amidolytic activity by extraction and clarification without Aerosil treatment

| pH extraction and clarification acetic acid | concentration of acetic acid after pH adjustment (mM) | IgG loss in filter cake (g L⁻¹ plasma) | IgG loss in PptG supernatant (g L⁻¹ plasma) | IgG loss Σ (g L⁻¹ plasma) | Precipitate G PKA (IU mg⁻¹) | fibrinogen (mg L⁻¹ plasma) | PL-1 (μmol mL⁻¹ g⁻¹) |
|---|---|---|---|---|---|---|---|
| 3.8 | 75 | 0.00 | 0.42 | 0.42 | 214 | 173 | 3.9 |
| 4.2 | 25 | 0.01 | 0.19 | 0.20 | 170 | 134 | 3.2 |
| 4.6 | 10 | 0.01 | 0.09 | 0.10 | 38 | 193 | 1.4 |
| 5.0 | 5 | 0.09 | 0.04 | 0.13 | 6.4 | 114 | 0.4 |
| 3.8 | 75 | 0.00 | 0.53 | 0.53 | 193 | 355 | 3.8 |
| 4.2 | 25 | 0.00 | 0.28 | 0.28 | 171 | 346 | 3.2 |
| 4.6 | 10 | 0.01 | 0.14 | 0.15 | 131 | 340 | 1.5 |
| 5.0 | 5 | 0.16 | 0.05 | 0.21 | 5.3 | 189 | <0.2 |

Consistent with the results found in Example 4, increasing the pH of the extraction/dissolution buffer to 5.0 resulted in a small increase in the IgG lost in the filter cake, however, this loss was more than offset by a larger decrease in the loss of IgG in the Ppt G supernatant.

Figure 2:
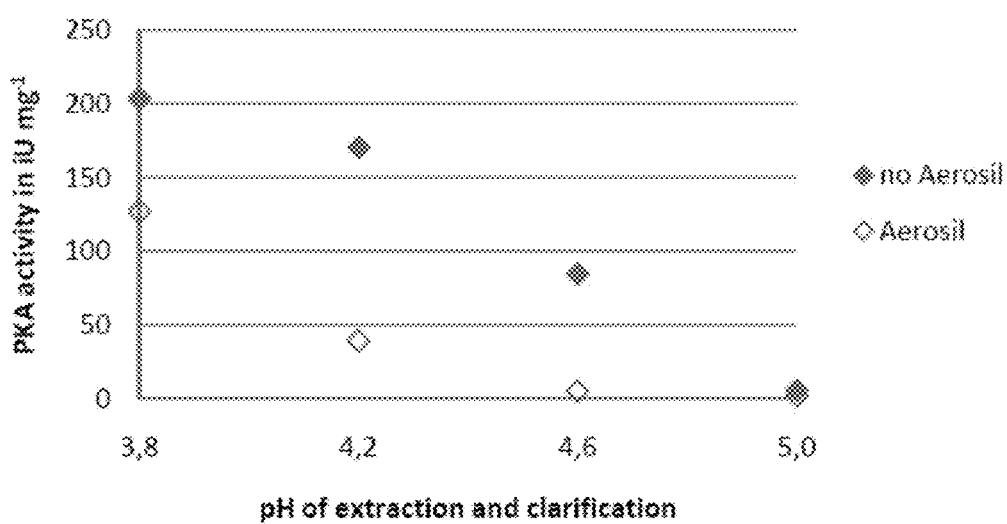
FIG. 2: Average PKA activity in Precipitate G dissolved fractions after extraction and clarification at pH 3.8 to 5.0 by addition of acetic acid in the presence and absence of Aerosil (silicon dioxide) treatment.
Figure 3:
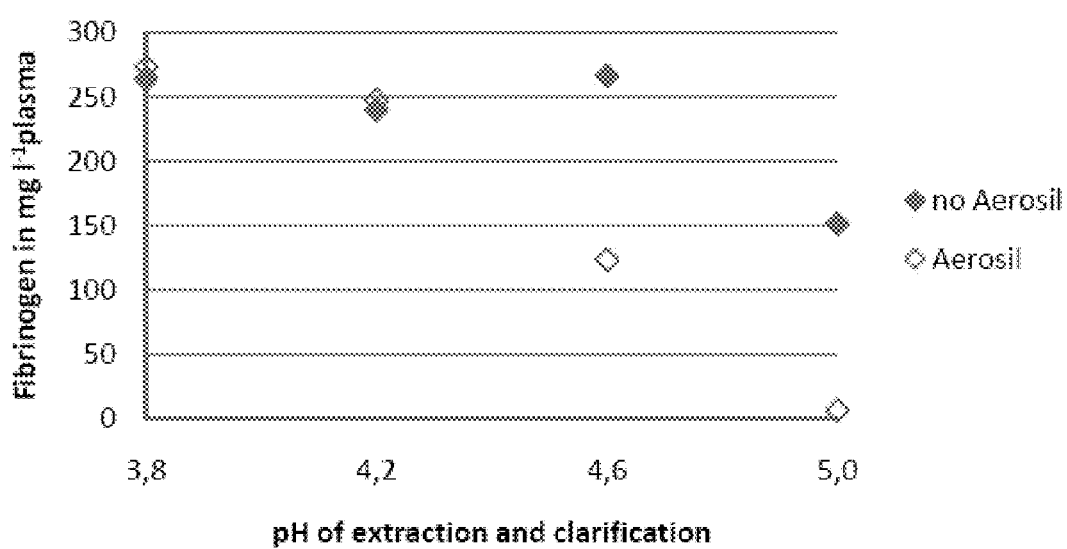
FIG. 3: Average fibrinogen content in Precipitate G dissolved fractions after extraction and clarification at pH 3.8 to 5.0 by addition of acetic acid in the presence and absence of Aerosil (silicon dioxide) treatment.
Figure 4:
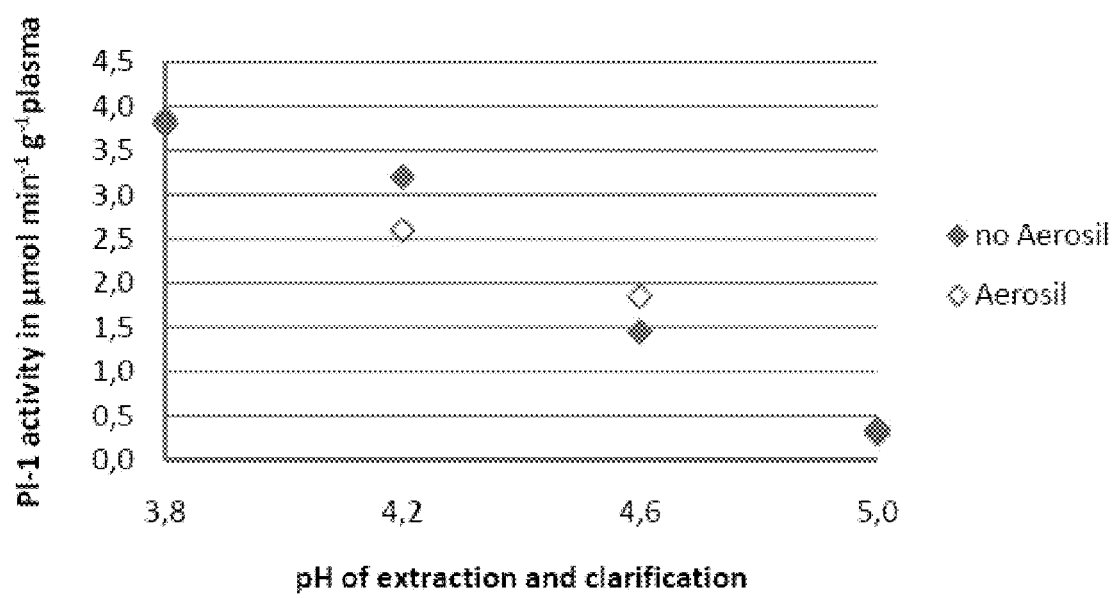
FIG. 4: Average amidolytic activity in Precipitate G dissolved fractions after extraction and clarification at pH 3.8 to 5.0 by addition of acetic acid in the presence and absence of Aerosil (silicon dioxide) treatment.

When the results of Example 4 and Example 5 are compared, it can be seen that Aerosil treatment reduces the amount of residual PKA activity found in the dissolved PptG fraction when the II+III paste is extracted at lower pHs (3.8, 4.2, and 4.6), but not at pH 5.0 (FIG. 2). Conversely, Aerosil treatment significantly reduces the fibrinogen content of the dissolved Ppt G fraction when the II+III paste is extracted at higher pHs (FIG. 3; compare pH 4.6 and 5.0 to pH 3.8 and 4.2). Aerosil treatment does not appear to affect the level of residual amidolytic activity found in the dissolved Ppt G fraction (FIG. 4). Notably, the level of all three contaminants in the dissolved Ppt G fraction is considerably reduced when the II+III paste is extracted at pH 5.0, as compared to pH 3.8, 4.2, and 4.6.

Example 6

As can be seen in the Examples above, IgG losses in the filter cake and Ppt G supernatants are minimized when the contaminants, while maintaining low levels of IgG loss in the filter cake and Ppt G supernatant.

Along these lines, extraction of modified II+III paste was performed as before, with extraction buffer having a pH of 4.5. Increasing amounts of Aerosil 380, up to 200 mg per g II+III paste, were then added and the suspension was stirred for one hour. Further processing of the sample was performed as above.

As can be seen in Table 6, both fibrinogen and PKA activity removal is significantly improved by clarification with high amounts of Aerosil. IgG losses in the filter cake due to binding onto Aerosil is increased with high amounts of Aerosil, although this effect was somewhat offset by a decrease in the loss of IgG in the Ppt G supernatant. Significantly, however, amidolytic activity could not be reduced by high amounts of Aerosil when the II+III paste is extracted at pH 4.5. Furthermore, although γ-globulin purity is improved with higher amounts of Aerosil, in all cases it is still below the specification limit of >86% for Ppt G. likely because of the low pH at the extraction and clarification.

TABLE 6

Table 6 gives the results of the variation in Aerosil concentration with extraction and clarification of pH 4.5

| amount of Aerosil in mg per gram II + III | IgG loss in filter cake (g L⁻¹ plasma) | IgG loss in PptG supernatant (g L⁻¹ plasma) | IgG loss Σ (g L⁻¹ plasma) | Precipitate G PKA (IU mg⁻¹) | fibrinogen (mg L⁻¹ plasma) | PL-1 (μmol mL⁻¹ g⁻¹) | CAE (% gamma globulin) |
|---|---|---|---|---|---|---|---|
| 0 | 0.01 | 0.21 | 0.22 | 177.1 | 272 | 5.4 | 69.1 |
| 40 | 0.13 | 0.50 | 0.63 | 9.3 | 173 | 1.8 | 76.8 |
| 100 | 0.11 | 0.30 | 0.41 | 0.1 | 76 | 6.1 | 79.4 |
| 200 | 0.25 | 0.08 | 0.33 | below det. Limit | 10 | 4.5 | 84.1 |

Example 7

The present example demonstrates the effect of the extraction buffer pH on the removal of impurities following II+III paste re-suspension and clarification.

Low pH extraction of modified II+III paste was performed at pH 4.2 using a ratio of 15 grams buffer per gram II+III paste. The suspension was then split into 3 parts and the pH adjusted to 4.5, 4.7, or 5.0 respectively with 3M Tris. Afterwards, each solution was further split into two parts, which were incubated for one hour at either 4° C. or 25° C. Filtration with Cuno 50(90)SA was performed using a 10 mM sodium acetate post-wash buffer having the same pH as the respective clarification buffer. The filtrates were treated with 8 g $L^{-1}$ citrate and 0.2% Tween 80, and then IgG was precipitated by addition of 25% ethyl alcohol at −10° C. for at least 8 hours.

The precipitate was recovered by centrifugation as described previously, and the precipitate was dissolved into a 2-fold volume of purified water. The resulting suspension was filtered using a Cuno VR06 filtration devise, in a final solution having a conductivity of about 1.3 mS $cm^{-1}$.

To evaluate the various conditions, the level of IgG, IgA, IgM, transferrin, fibrinogen, and other impurities were determined. The results of this analysis are given in Table 7, which shows the pH dependency of clarification of II+III paste suspension. Within the pH range of 4.5 to 5.0 IgA, IgM, transferring, and fibrinogen amount does not vary in a wide range, but other unwanted proteins are present at a higher levels when the lower pH buffers are used. It was calculated that these other impurities comprise 10% of the total protein at pH 4.5, but less than 1% at pH 5. The IgG content is the highest at pH 5.0, while the temperature dependence of IgG content and impurity levels, between 4° C. and 25° C., is negligible.

TABLE 7

Table 7 compares the reduction of impurities from II + III dissolved to VR06 filtrate by variation in pH and temperature during 1 hour incubation after re-suspension of II + III paste and subsequent filtration after low pH extraction without additives

| pH of incubation and both filtration steps | temperature of incubation and first filtration step | step | % of Protein ||||||
|---|---|---|---|---|---|---|---|---|
| | | | IgG nephelometric | IgA ELISA | IgM ELISA | transferrin ELISA | fibrinogen ELISA | calculated other impurities |
| 4.5 | 4° C. | II + III dissolved | 55.0 | 7.9 | 3.6 | 1.3 | 3.0 | 29.3 |
| | | Cuno 90-filtrate | 51.7 | 8.5 | 4.0 | 1.6 | 2.5 | 31.7 |
| | | Ppt G dissolved | 64.4 | 8.3 | 4.4 | 0.1 | 2.8 | 20.0 |
| | | VR06-filtrate | 71.8 | 9.5 | 5.1 | 0.1 | 3.0 | 10.6 |
| | 25° C. | II + III dissolved | 55.0 | 7.9 | 3.6 | 1.3 | 3.0 | 29.3 |
| | | Cuno 90-filtrate | 52.3 | 8.0 | 4.2 | 1.6 | 2.6 | 31.3 |
| | | Ppt G dissolved | 64.5 | 7.4 | 4.8 | 0.1 | 3.8 | 19.4 |
| | | VR06-filtrate | 72.5 | 9.1 | 5.0 | 0.1 | 3.3 | 9.9 |
| 4.7 | 4° C. | II + III dissolved | 55.0 | 7.9 | 3.6 | 1.3 | 3.0 | 29.3 |
| | | Cuno 50-filtrate | 49.4 | 8.2 | 3.7 | 1.6 | 2.5 | 34.6 |
| | | Ppt G dissolved | 68.8 | 9.5 | 5.0 | 0.1 | 3.5 | 13.2 |
| | | VR06-filtrate | 76.5 | 9.8 | 5.4 | 0.1 | 3.5 | 4.7 |
| | 25° C. | II + III dissolved | 55.0 | 7.9 | 3.6 | 1.3 | 3.0 | 29.3 |
| | | Cuno 50-filtrate | 49.6 | 8.6 | 3.7 | 1.5 | 3.1 | 33.6 |
| | | Ppt G dissolved | 66.9 | 8.8 | 4.9 | 0.1 | 4.1 | 15.2 |
| | | VR06-filtrate | 75.8 | 10.2 | 5.3 | 0.1 | 4.3 | 4.3 |
| 5.0 | 4° C. | II + III dissolved | 55.0 | 7.9 | 3.6 | 1.3 | 3.0 | 29.3 |
| | | Cuno 50-filtrate | 52.5 | 9.3 | 3.4 | 1.7 | 2.1 | 31.0 |
| | | Ppt G dissolved | 76.9 | 10.1 | 4.9 | 0.1 | 3.0 | 5.0 |
| | | VR06-filtrate | 83.6 | 10.6 | 4.5 | 0.1 | 3.0 | 0.0 |
| | 25° C. | II + III dissolved | 55.0 | 7.9 | 3.6 | 1.3 | 3.0 | 29.3 |
| | | Cuno 50-filtrate | 53.4 | 8.9 | 3.4 | 1.8 | 2.6 | 30.0 |
| | | Ppt G dissolved | 76.6 | 10.3 | 4.8 | 0.1 | 3.9 | 4.3 |
| | | VR06-filtrate | 79.9 | 10.9 | 4.7 | 0.1 | 3.6 | 0.8 |

As can be seen in Table 8, further analysis of the dissolved Ppt G fraction and VR06-filtrate indicate that use of buffers having a pH of 4.5 for the II+III clarification and II+III filtrate treatment steps, results in increased level of aggregates and low molecular weight components. This effect is further enhanced when the steps are performed at 25° C., rather than 4° C. Conversely, when the samples are treated at higher pH (pH 5.0), the resulting Ppt G suspensions and filtrate contain higher levels of ~350 kDa material (dimeric IgG or IgA) than do the solutions treated at pH 4.5 (Table 8). Furthermore, the lower pH treatments resulted in higher amidolytic activity levels than did treatment at pH 5.0.

TABLE 8

Influence of pH and temperature during incubation and filtration of II + III paste suspension on PKA and amidolytic activities of Precipitate G dissolved and on the molecular size distribution in VR06 filtrate.

| pH of incubation and both filtration steps | temperature of incubation and first filtration step | Ppt G dissolved | | | VR06-filtrate molecular size distribution (%) | | | |
|---|---|---|---|---|---|---|---|---|
| | | PKA activity | amidolytic activity (PL-1) | | | | | |
| pH | temp. °C. | IU mL$^{-1}$ | IU g$^{-1}$ | nmol mL$^{-1}$·min$^{-1}$ | nmoL min$^{-1}$·g$^{-1}$ | >450 kDa | ~350 kDa | ~160 kDa | <60 kDa |
| 4.5 | 4 | 60.2 | 2028 | 171.8 | 5788 | 28.33 | 6.61 | 63.21 | 1.85 |
| 4.5 | 25 | 103.4 | 3569 | 239.4 | 8264 | 29.44 | 6.02 | 61.76 | 2.79 |
| 4.7 | 4 | 1343.2 | 38029 | 152.1 | 4306 | 23.71 | 8.82 | 65.82 | 1.64 |
| 4.7 | 25 | 2215.9 | 67702 | 180.2 | 5506 | 24.54 | 8.02 | 65.06 | 2.38 |
| 5.0 | 4 | 134.5 | 4009 | 67.6 | 2015 | 17.81 | 10.78 | 70.03 | 1.38 |
| 5.0 | 25 | 186.6 | 5738 | 87.3 | 2685 | 19.16 | 10.54 | 68.84 | 1.46 |

Example 8

The results presented in Tables 7 and 8 show that the re-suspension of II+III precipitate should be performed at refrigerated temperatures (2° C. to 8° C.) and that pH should be kept at pH 5.0 in order to minimize dissolution of high (>450 KDa) and low (>70 KDa) molecular weight components, as well as components having amidolytic activity. Effective clarification after II+III paste suspension will reduce the impurity load for chromatography downstream processing of Ppt G and is therefore key for meeting the IVIG final container specifications reproducibly. To further validate this finding, modified II+III paste was dissolved and processed, as above, the modified II+III paste was dissolved at pH 4.2 and then adjusted to pH of 4.5, 4.7, or 5.0. As seen in Table 9, IgM is removed more efficiently by a pH of 5.0 during II+III paste suspension and clarification than removal at pH 4.5. In this experiment IgG yield is similar at pH 5.0 and 4.5.

TABLE 9

IgG, IgA, IgM, transferrin and fibrinogen yield at various steps of II + III paste re-suspension, filtration and Ppt G precipitation

| pH of incubation and both filtration steps | temperature of incubation and first filtration step | step | yield % | | | | | |
|---|---|---|---|---|---|---|---|---|
| | | | total protein | IgG neph./ELISA[1] | IgA ELISA | IgM ELISA | transferrin ELISA | fibrinogen ELISA |
| 4.5 | 4° C. | II + III dissolved | 100.0 | 100.0 | 100.0 | 100.0 | 100.0 | 100.0 |
| | | Cuno 50 filtrate | 100.2 | 92.9 | 100.2 | 97.8 | 118.7 | 86.3 |
| | | Cuno 90 filtrate | 97.0 | 91.1 | 105.3 | 108.6 | 123.2 | 80.1 |
| | | Ppt G supernatant | 33.5 | 4.4 | — | — | — | — |
| | | Ppt G dissolved | 71.7 | 83.9 | 75.6 | 89.6 | 5.0 | 66.5 |
| | | VR06 filtrate | 65.3 | 85.2 | 78.8 | 93.1 | 5.2 | 64.8 |
| | 25° C. | II + III dissolved | 100.0 | 100.0 | 100.0 | 100.0 | 100.0 | 100.0 |
| | | Cuno 50 filtrate | 101.0 | 92.3 | 100.9 | 104.4 | 113.2 | 96.7 |
| | | Cuno 90 filtrate | 97.2 | 92.4 | 98.9 | 113.4 | 123.9 | 84.6 |
| | | Ppt G supernatant | 33.8 | 5.1 | — | — | — | — |
| | | Ppt G dissolved | 72.9 | 85.5 | 68.8 | 97.5 | 4.7 | 89.9 |
| | | VR06 filtrate | 68.3 | 90.0 | 78.9 | 95.9 | 5.5 | 75.0 |
| 4.7 | 4° C. | II + III dissolved | 100.0 | 100.0 | 100.0 | 100.0 | 100.0 | 100.0 |
| | | Cuno 50 filtrate | 93.5 | 83.9 | 98.0 | 98.0 | 115.9 | 75.3 |
| | | Ppt G supernatant | 27.5 | 2.7 | — | — | — | — |
| | | Ppt G dissolved | 64.8 | 81.1 | 78.2 | 90.2 | 4.5 | 73.9 |
| | | VR06 filtrate | 60.5 | 84.1 | 75.0 | 92.1 | 5.1 | 70.2 |
| | 25° C. | II + III dissolved | 100.0 | 100.0 | 100.0 | 100.0 | 100.0 | 100.0 |
| | | Cuno 50 filtrate | 94.7 | 85.3 | 103.1 | 98.5 | 113.8 | 95.8 |
| | | Ppt G supernatant | 28.5 | 4.1 | — | — | — | — |
| | | Ppt G dissolved | 65.3 | 79.5 | 73.1 | 90.9 | 5.0 | 87.0 |
| | | VR06 filtrate | 61.9 | 85.3 | 80.7 | 93.0 | 5.3 | 86.9 |
| 5.0 | 4° C. | II + III dissolved | 100.0 | 100.0 | 100.0 | 100.0 | 100.0 | 100.0 |
| | | Cuno 50 filtrate | 86.1 | 82.3 | 101.5 | 81.5 | 117.5 | 59.8 |
| | | Ppt G supernatant | 26.0 | 4.1 | — | — | — | — |
| | | Ppt G dissolved | 58.1 | 81.2 | 74.8 | 79.3 | 4.5 | 57.0 |
| | | VR06 filtrate | 54.0 | 82.1 | 72.5 | 67.8 | 4.7 | 52.5 |
| | 25° C. | II + III dissolved | 100.0 | 100.0 | 100.0 | 100.0 | 100.0 | 100.0 |
| | | Cuno 50 filtrate | 88.0 | 85.4 | 99.7 | 83.2 | 124.1 | 75.4 |
| | | Ppt G supernatant | 23.4 | 1.5 | — | — | — | — |
| | | Ppt G dissolved | 60.5 | 84.2 | 79.0 | 81.6 | 4.5 | 78.2 |
| | | VR06 filtrate | 59.0 | 85.7 | 82.0 | 77.6 | 4.5 | 69.0 |

Example 9

Figure 5:
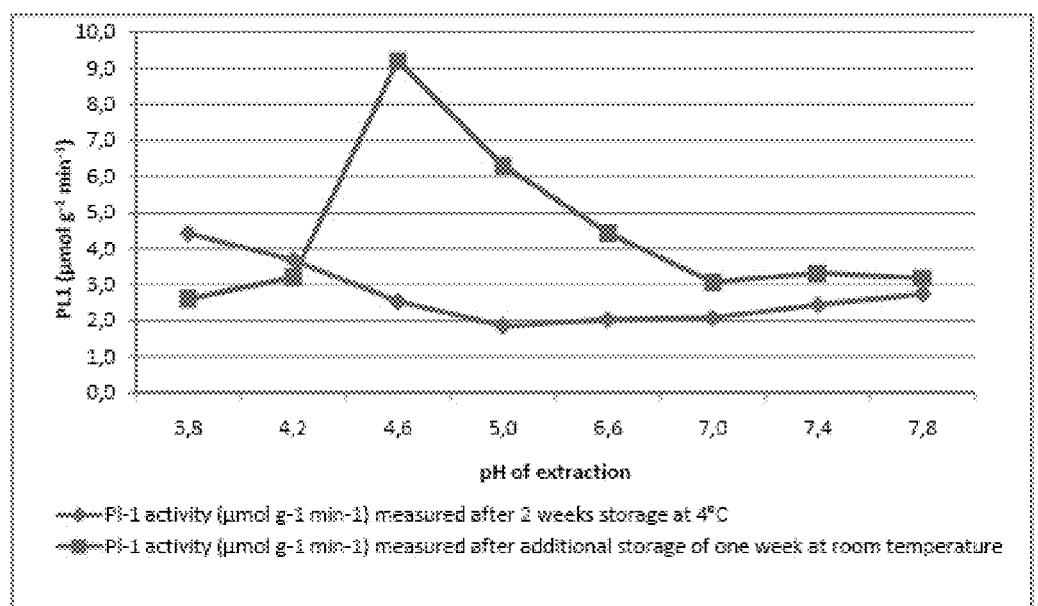
FIG. 5: Amidolytic activity in Precipitate G dissolved fractions extracted and clarified at pH 3.8 to 7.8 after incubation for two weeks at 4° C. (♦) or for an additional week at room temperature (■).
Figure 6:
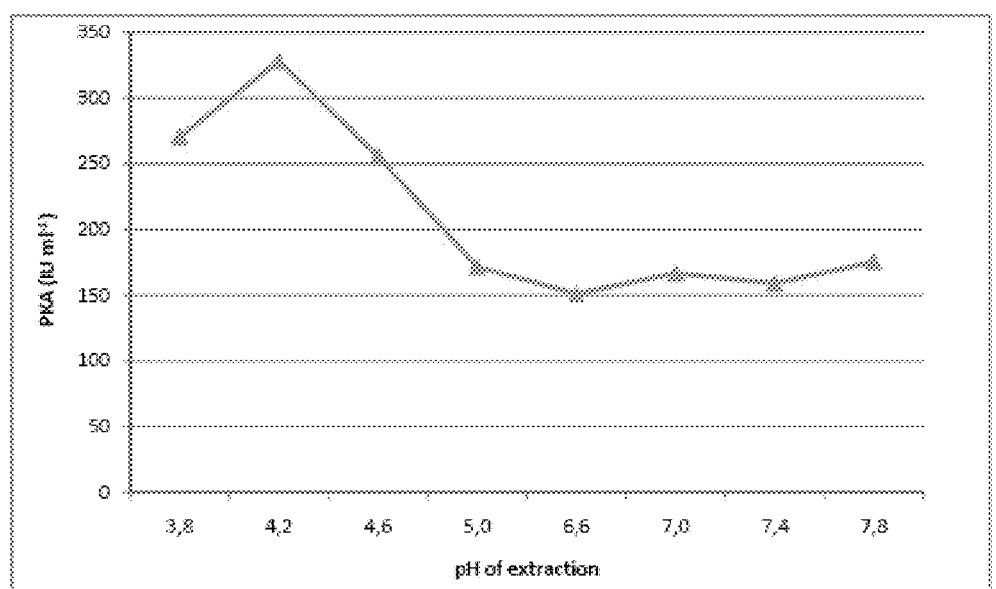
FIG. 6: PKA activity in Precipitate G dissolved fractions extracted and clarified at pH 3.8 to 7.8.

To evaluate the pH optimum at the II+III paste extraction step, for minimized proteolytic activities in the filtrate, pH during extraction and filtration was varied in a wider range from pH 3.8 to 7.8. For this purpose modified II+III paste was extracted at low pH in a ratio of 1+8. After a short time of stirring, to obtain a homogeneous dispersion, the suspension was divided into 8 parts, the pH adjusted with acetic acid or Tris buffer to either pH 3.8, 4.2, 4.6, 5.0, 6.6, 7.0, 7.4 or 7.8, and extracted for an additional 120 minutes. Afterwards, pH was adjusted to 5.1 and clarification was done by centrifugation in 50 mL Falcon tubes. Ppt G precipitation was performed under standard conditions. Amidolytic activity and PKA was measured in the Ppt G dissolved fraction as indicated in FIGS. 5 and 6.

Example 10

The present example evaluates the pH dependency on IgG yield loss during extraction and clarification. Briefly, 110 grams of modified II+III paste was re-suspended at ratio of 15 grams purified water per gram II+III paste, followed by extraction for 120 minute. The sample was then divided into four parts and the pH adjusted with acetic acid to pH 3.8, 4.2, 4.6, or 5.0. Pre-extraction was done before dividing into four parts at native pH to ensure four identical parts which were then adjusted to the mentioned pH and further extracted for one additional hour. Samples were then clarified by Cuno 50SA filtration at the same pH used for each extraction and Ppt G precipitation. After Cuno filtration, all parts were treated the same way, which means standard precipitate G precipitation at pH 7.0 for all parts. The results of two such experiments are summarized below in Tables 10 and 11.

TABLE 10

Protein and IgG recoveries in the filtrates as well as the MSD and CAE results of the re-dissolved Precipitate G's

| | | | 38/1 | | | | 41 | | | |
|---|---|---|---|---|---|---|---|---|---|---|
| | | | pH extraction and clarificaion | | | | | | | |
| | | | 3.8 | 4.2 | 4.6 | 5.0 | 3.8 | 4.2 | 4.6 | 5.0 |
| | | | concentration of acetic acid after pH adjustment | | | | | | | |
| | | | 75 | 25 | 10 | 5 | 75 | 25 | 10 | 5 |
| | filtrate | protein recovery (%) | 100.3 | 99.6 | 92.8 | 76.0 | 106.4 | 107.5 | 99.7 | 81.0 |
| | | IgG recovery (%) | 87.6 | 89.8 | 90.3 | 86.0 | 96.2 | 97.3 | 95.1 | 88.3 |
| Precipitate G | MSD (% area) | >450 kDa | 19.2 | 20.5 | 14.8 | 13.2 | 22.5 | 22.8 | 20.7 | 16.8 |
| | | ~350 kDa | 8.7 | 7.6 | 10.5 | 11.7 | 5.2 | 5.0 | 7.7 | 9.4 |
| | | ~160 kDa | 69.5 | 69.2 | 72.9 | 74.2 | 66.0 | 65.6 | 67.5 | 72.0 |
| | | <70 kDa | 2.7 | 2.7 | 1.8 | 1.0 | 62 | 5.6 | 4.1 | 1.9 |
| | CAE (% gamma globulin) | | 67.4 | 68.3 | 78.1 | 86.7 | 68.3 | 69.8 | 77.5 | 85.1 |

TABLE 11

IgG loss during extraction and clarification as well as proteolytic activities and fibrinogen in the re-dissolved Precipitate G

| pH extraction and clarification acetic acid | concentration of acetic acid after pH adjustment (mM) | IgG loss in filter cake (g L$^{-1}$ plasma) | PptG supernatant (g L$^{-1}$ plasma) | IgG loss Σ (g L$^{-1}$ plasma) | PKA (IU mg$^{-1}$) | fibrinogen (mg L$^{-1}$ plasma) | PL-1 (μmol mL$^{-1}$ g$^{-1}$) |
|---|---|---|---|---|---|---|---|
| 3.8 | 75 | 0.00 | 0.42 | 0.42 | 214 | 173 | 3.9 |
| 4.2 | 25 | 0.01 | 0.19 | 0.20 | 170 | 134 | 3.2 |
| 4.6 | 10 | 0.01 | 0.09 | 0.10 | 38 | 193 | 1.4 |
| 5.0 | 5 | 0.09 | 0.04 | 0.13 | 6.4 | 114 | 0.4 |
| 3.8 | 75 | 0.00 | 0.53 | 0.53 | 193 | 355 | 3.8 |
| 4.2 | 25 | 0.00 | 0.28 | 0.28 | 171 | 346 | 3.2 |
| 4.6 | 10 | 0.01 | 0.14 | 0.15 | 131 | 340 | 1.5 |
| 5.0 | 5 | 0.16 | 0.05 | 0.21 | 5.3 | 189 | 0.2 |

As can be seen in the sample stored at 4° C. in FIG. 5, amidolytic activity is minimized when the II+III paste is extracted at pH 5.0. Further emphasizing the point that the samples should not be kept at elevated (room temperature) for extended periods of time, amidolytic activity was elevated after storage of the Ppt G dissolved fraction at room temperature for one week. Similarly, as seen in FIG. 6, PKA activity is minimized when the II+III paste is extracted at pH 5.0 or higher.

The data above confirms the results shown in FIGS. 5 and 6 concerning the activation of proteolytic enzymes by low pH extraction. Taken together, the data demonstrate that low pH extraction causes less IgG loss due to the increased solubility of all proteins. These results are consistent with the examples provided above. Additionally, the IgG losses shown in Table 11 suggest that higher concentrations of acetic acid, resulting in lower pH, results in less IgG loss in the filter cake but higher IgG loss in Precipitate G supernatant. This phenomenon might be explained by the higher acetate concentrations at the precipitation step after low pH extraction.

Example 11

To determine suitable II+III extraction conditions, a protocol employing low pH extraction with purified water adjusted with acetic acid to pH 4.3 and readjustment to pH 4.9 before filtration was compared with extraction in 5 mM sodium acetate/5 mM sodium di-hydrogen phosphate with 600 g acetic acid per 1000 liter of extraction buffer, resulting in a dissolution pH of 4.8 to 4.9. The experiments were performed in pilot scale, starting with 3.8 to 5 kg of modified II+III paste. All experiments included Aerosil treatment with 40 g Aerosil per kg II+III paste. For clarification, a Strassburger filter press with filter frames of 30 cm*30 cm equipped with Cuno 50SA filter sheets was used. Post wash was performed with 4 dead volumes of the filter press, with a 5 mM sodium acetate/5 mM sodium di-hydrogen phosphate buffer with 150 gram acetic acid per 1000 liter of buffer. Centrifugation of precipitate G was performed with a Cepa® Z61H centrifuge at 17000 RPM (rotor diameter of 10.5 cm) at a flow rate of 40 liter per hour. The results of the experiment, done in triplicate, is shown in Table 12.

Example 12

During manufacturing, filter press frames and lines connecting to and from the tanks have a significant void volume, which is still filled with suspension or filtrate before post-wash is started. When the post wash is finished this void volume remains in the filter press. Standard protocols account for this void volume by washing with between one and two dead volumes of the filter press. In order to determine if standard post-filter washes allow for efficient recovery of total IgG, experiments using varying volumes of wash buffer were performed on large-scale manufacturing IgG purifications. FIG. 1 shows the dependency of post-wash volumes (as measured by dead or void volumes) on the levels of residual IgG and total protein.

Notably, as seen in FIG. 1, a post-filtration wash using about 2-fold filter press dead volume results in significant loss of IgG recovery, as the wash solution contains about 1.5 gram IgG per L wash solution. Surprisingly, it was found that 3.6-fold filter press dead volume of post-wash buffer is required for efficient recovery of IgG (denoted by arrow in FIG. 1). Further post-washing beyond 3.6 dead volumes of

TABLE 12

Comparison of low pH extraction at pH 4.3 and shift of pH to 4.9 prior to Aerosil treatment with extraction by improved GAMMAGARD ® LIQUID conditions with 600 g glacial acetic acid per 1000 L of extraction buffer

| | | experiment | | | | | |
|---|---|---|---|---|---|---|---|
| | | P000609NG2 | P00909NG2 | P01509NG2 | P02209NG2 | P02509NG2 | P02609NG2 |
| | | | | method | | | |
| | | low pH-extraction | | | 600 g HAc per 1000 L extractionbuffer | | |
| | | | | Lot# | | | |
| | unit | VNEGJ039 | VNGBJ022 | VNGBJ216 | VNGBJ216 | VNGBJ022 | VNEGJ039 |
| II + III-paste | kg | 5.00 | 5.00 | 4.97 | 4.96 | 4.96 | 3.88 |
| PEQ | L | 106.65 | 118.70 | 123.32 | 123.31 | 117.65 | 82.35 |
| | | | | II + III-extract | | | |
| protein | g | 1316 | 1310 | 1364 | 1336 | 1347 | 1022 |
| protein yield (BIURET) | g L$^{-1}$ | 12.3 | 11.0 | 11.1 | 10.8 | 11.5 | 12.4 |
| IgG yield (ELISA) | g L$^{-1}$ | 6.09 | 5.89 | 6.25 | 5.50 | 6.06 | 6.35 |
| IgA yield (ELISA) | g L$^{-1}$ | 1.06 | 0.96 | 0.98 | 1.00 | 1.01 | 1.10 |
| IgM yield (ELISA) | g L$^{-1}$ | 0.40 | 0.40 | 0.47 | 0.40 | 0.43 | 0.48 |
| | | | | filtrate | | | |
| protein | g | 957 | 1007 | 1038 | 955 | 926 | 731 |
| protein yield (BIURET) | g L$^{-1}$ | 9.0 | 8.5 | 8.4 | 7.7 | 11.5 | 12.4 |
| IgG yield (ELISA) | g L$^{-1}$ | 5.7 | 5.62 | 5.45 | 5.02 | 6.06 | 6.38 |
| IgA yield (ELISA) | g L$^{-1}$ | 1.03 | 0.86 | 0.96 | 0.90 | 1.01 | 1.10 |
| IgM yield (ELISA) | g L$^{-1}$ | 0.32 | 0.39 | 0.37 | 0.27 | 0.43 | 0.48 |
| | | | | filtercake extract | | | |
| IgG yield (ELISA) | g L$^{-1}$ | — | — | — | 0.07 | 0.07 | 0.07 |
| | | | | Ppt G-supernatant | | | |
| protein | g | 196 | 130 | 188 | 187 | 168 | 109 |
| protein yield (BIURET) | g L$^{-1}$ | 1.8 | 1.1 | 1.5 | 1.5 | 1.4 | 1.3 |
| IgG yield (ELISA) | g L$^{-1}$ | 0.05 | 0.02 | 0.03 | 0.05 | 0.03 | 0.04 |

As seen in Table 12, both extraction protocols result in similar IgG recoveries. Given the results of Examples 3 through 10, which show that various impurities can be minimized by extraction of II+III paste at pH 5.0, the results provided in Table 12 show that extraction at pH 4.8 to 4.9 with 600 g glacial acetic acid per 1000 L of extraction buffer is superior to extraction at low pH and subsequent adjustment to pH 4.8 to 5.0.

the filter press is not expedient, as it will lead to dilution of the filtrate without additional IgG recovery.

Example 13

During the II+III precipitation step, alcohol concentration was increased from 20 to 25% and the temperature was lowered from −5° C. to −7° C. When dissolving the II+III paste, at least 600 mL glacial acetic acid was used per 1000 L volume to adjust pH of II+III paste re-suspension buffer, in contrast to previously use ratio of 510 mL glacial acetic acid/1000 L buffer. The extraction ratio was 1+15 with the acetic acid buffer. For clarification, 0.04 to 0.06 gram of Aerosil (typically at the low end of this range, e.g., 0.04 g) was added for each gram of II+III paste. For post-wash, about four (4×) filter press dead volumes of post-wash buffer was used. For example, 4.3× filter press dead volumes was used in one particular experiment whereas 3.6× volumes was used in another experiment. The four times or more dead volumes post-wash was increased from previously used 1.8× dead volumes. The buffer was adjusted with 150 mL glacial acetic acid was used per 1000 L buffer, an increase from previously 120 mL glacial acetic acid/1000 L buffer. These changes led to an 8% higher yield of IgG and a purity of at least 86% γ-globulin. Very low residual amount of IgG was found in the filter cake extract, when extracted with 0.1 M sodium phosphate+150 mM NaCl (pH 7.4, conductivity 25.5 mS/cm).

Example 14

A. Optimization of Fractionation I: Ethanol Addition by Spraying Versus Fluent-Wise Addition; pH Adjustment to pH 7.0 or 7.5 After Ethanol Addition Table 13 shows IgG yield by the manufacturing methods currently in use and provides a comparison reference in the experiments described below. 15-20% of IgG is lost from Cohn pool to filtrate. About 0.4 g IgG per liter plasma is lost in the II+III supernatant.

TABLE 13

| | IgG Yield (2009) | | | | | |
|---|---|---|---|---|---|---|
| | g/L plasma | | | % of Cohn pool | | |
| Fraction | LA B1 (source) | Vienna (source) | LA B5 (Rec.) | L.A. (source) | Vienna (source) | L.A. (Rec.) |
| Cohn pool | 6.18 (5.28-7.02) | 6.26 (5.43-6.68) | 7.49* (6.41-8.41) | 100 | 100 | 100 |
| II + III Supernatant | 0.41 (0.23-0.63) | 0.39 (0.33-0.47) | 0.37 (0.23-0.48) | 6.6 | 6.2 | 4.9 |
| II + III precipitate (calculated) | 5.77 | 5.87 | 7.12 | 93.4 | 93.8 | 95.1 |
| II + III filtrate | 4.93 (4.21-5.57) | 5.19 (4.11-5.48) | 6.43 (6.11-7.02) | 80 | 83 | 86 |

*LA B5 recovered plasma Cohn pool: lower IgG concentration due to saline chase. Average LA B1 recovered plasma Cohn pool: 8.52 g/L.

Method

Cohn pool was thawed at 24-27° C. for 6-7 hours in a 14-liter bucket. Afterwards the material was mixed overnight at 2-8° C. The pool was then divided into four parts (800 g each):

1: Fluent-wise ethanol addition, followed by pH adjustment to 7.0
2: Fluent-wise ethanol addition, followed by pH adjustment to 7.5
3. Ethanol addition by spraying, followed by pH adjustment to 7.0
4. Ethanol addition by spraying, followed by pH adjustment to 7.5

All parts were first cooled to 0° C. 8% ethanol was then added to parts 1 and 2 fluent-wise and by spraying to parts 3 and 4 using a spray head. In both methods ethanol was added at approximately the same speed. During ethanol addition, the cryostat was adjusted to −5° C. and 75 ml ethanol was added to each part while mixing. The pH was adjusted to either 7.0 or 7.5 by 1M acetic acid. The solution was then incubated for 1 hour. After the incubation the solution was centrifuged with a beaker centrifuge (4600 rpm; 30 min; −2° C.).

Results

IgG yields were measured nephelometrically and are shown in Table 14. Almost 100% IgG yield in the fractionation I supernatant was obtained with the improved method (ethanol spraying) while with conventional ethanol addition 0.2 to 0.25 g/L plasma was lost. These results indicate that the improved method may lead to an increase of IgG yield of up to 0.2 g/L plasma in manufacturing.

TABLE 14

| | | IgG neph (mean of 3) | | | | |
|---|---|---|---|---|---|---|
| Sample | Weight (g) | mg/ml | g | % | Purity (%) | g/L Plasma |
| Cryo-poor Plasma | 800 | 5.72 | 4.57 | 100.00 | 12.2 | 5.72 |
| Supernatant 1 | 856 | 5.10 | 4.37 | 95.57 | 12.6 | 5.46 |
| Supernatant 2 | 853 | 5.16 | 4.41 | 96.36 | 12.7 | 5.51 |
| Supernatant 3 | 853 | 5.36 | 4.58 | 100.14 | 13.1 | 5.72 |
| Supernatant 4 | 848 | 5.33 | 4.52 | 98.90 | 13.0 | 5.65 |

B. Pilot Scale: Fractionation I (Spray V. Fluent-Wise; pH Adjustment to 7.4 after Ethanol Addition) and Fractionation II+III (pH Adjustment to 6.7 Before Ethanol Addition, Readjustment to 6.9 after Ethanol Addition)

Example 15

Method 2.8 kg plasma was thawed while mixing at 2° C. Fraction I: 8% ethanol was added and the pH was adjusted to 7.4 using 5 M acetic acid. While mixing, the suspension was cooled to a temperature of −2° C. Spraying conditions were obtained using a spray head. In both methods ethanol and 5 M acetic acid addition was performed at approximately the same speed. After 1 hour incubation, the solution was centrifuged using a CEPA centrifuge at a temperature of −4° C.

Fraction II+III:

pH was adjusted to 6.7 using a pH 4 buffer, then 25% ethanol was added (1) by spraying or (2) by fluent-wise as conventionally performed. The pH was then readjusted to 6.9. Incubation was conducted for 10 hours at −7° C.

Results

IgG loss during fraction II+III at 25% ethanol was measure nephelometrically and is shown in Table 15. The IgG measurements had a certain variation, the average value of the optimized method were therefore taken.

TABLE 15

| Experiment | IgG Loss Fraction I g per liter plasma | Fraction II + III supernatant, 25% ethanol added g per liter plasma | IgG in the filtrate % of Cohn pool |
|---|---|---|---|
| NG2C73 | 0.47 | 0.08 | 85.28 |
| NG2C73-1 | 0.34 | 0.03 | 92.27 |
| NG2C73-2 | 0.05 | 0.06 | 95.94 |
| Average | 0.29 | 0.06 | 91.16 |
| Reference (ethanol addition Fluent-wise) | 0.29 | 0.10 | 87.38 |

Up to the point of fraction II+III precipitate only 0.35 g IgG/L plasma was lost. A yield increase of 0.04 g IgG per liter plasma during fractionation II+III using spraying method was achieved, compared to 25% ethanol addition fluent-wise; and a yield increase of 0.3 g IgG per liter plasma was achieved (averaged from the range of 0.4 to 0.06 g/L), compared to 20% ethanol addition fluent-wise as currently used in manufacturing. The IgG yield in the filtrate is significantly higher compared to the reference and far above the 80 to 86% achieved currently in manufacturing with addition of 20% ethanol fluent-wise at II+III precipitation.

C. Fractionation II+III (20% Ethanol): Maintain Initial pH all Over Fractionation II+III Example 16

Method 50 liter plasma was thawed while mixing at 17-20° C. for 27 hours. Fractionation I was performed as mentioned in the above sections as the optimized process. Supernatant I was separated into two parts:
(1) worst case pH adjustment: pH adjustment before and after ethanol addition but not during incubation period.
(2) optimized pH adjustment: pH adjustment before and after ethanol addition and further readjustment of the pH during hold time. The solution was constantly stirred during hold time.

pH of the supernatant of I was adjusted in both parts to 6.7 before ethanol addition using pH 4 buffer. Ethanol was added by spraying and pH was readjusted to 6.9 after ethanol addition.

In part (1) the pH adjustment was carried out with less care to simulate a worst case scenario. pH of the solution was adjusted directly after ethanol addition but not during the incubation. In part (2) the pH was readjusted to a constant value of 6.8 to 7.0 during incubation time of 10 hours.

Results

IgG was again measure nephelometrically and is shown in Table 16. By constant readjustment of the pH to a constant value of about 6.9 during the hold time, only 0.13 g IgG per liter plasma was lost compared to an average of 0.4 g/L plasma in large-scale manufacturing. Yield increase of 0.07 g IgG per liter plasma was achieved in comparison to reference (without spraying but with constant stirring during hold period). Yield increase of about 0.20 g to about 0.30 g IgG per liter plasma was achieved compared to the conventional method currently in use (loss of 0.38 g IgG per liter plasma, see Table 13).

TABLE 16

| | | Volume | IgG measured nephelometrically | |
|---|---|---|---|---|
| | Sample | kg | Yield (%) | g/L plasma |
| Pool | Plasma | 45.20 | 100.00 | 4.90 |
| Fraction I | Supernatant I | 68.66 | 102.61 | 5.03 |
| Optimized pH adjustment | Supernatant II + III | 53.09 | 0.26 | 0.13 |
| Reference | Supernatant II + III | 52.69 | 0.41 | 0.20 |

Conclusion

IgG loss in II+III supernatant is reduced from the current level of 0.4 g IgG/L plasma in manufacturing batches to a level of 0.13 g/L plasma at precipitation with 20% ethanol, and to a level of less than 0.08 g/L plasma at precipitation with 25% ethanol when ethanol is added by spraying and a continuous pH of 6.9±0.1 is maintained during precipitation.

At precipitation I, ethanol addition before pH adjustment by spraying leads to an IgG yield increase of 0.1 to 0.2 g/L plasma in fractionation I supernatant.

Discussion

IgG was measured nephelometrically in all experiments and can have a variance of at least −/+5.0% (as indicated by the manufacturer of the nephelometer, Siemens AG). It is therefore possible that the actual yield increase obtained by the improved method during manufacturing may be slightly lower or higher than indicated in the examples.

As additional proof of the yield increase by the new and improved method, the precipitate IgG weight was compared to the average precipitate IgG weight obtained from the same plasma source in manufacturing. 18 kg precipitate IgG is obtained per 1000 liter US source Cohn Pool by the method currently used in manufacturing, in contrast to the pilot scale study (section B above) where 20.8 kg precipitate IgG was obtained (20% ethanol and optimized pH adjustment at fractionation II+111, all buffer and ethanol addition by spraying). This is an increase of more than 2 kg precipitate IgG per 1000 liter Cohn Pool.

Example 17

This example demonstrates that the addition of a fumed silica treatment step prior to filtration of the Fraction II+III suspension results in higher purity IgG filtrates. Briefly, cryopoor plasma was fractionated as described above to the Fraction II+III stage, at which point it was split into two samples. The first sample was clarified only by addition of filter aid prior to standard Fraction II+III suspension filtration (FIG. 7A). the second sample was subjected to fumed silica pretreatment, as described herein, prior to addition of filter aid and standard Fraction II+III suspension filtration (FIG. 7B).

The protein components of the filtrates were then separated by cellulose acetate electrophoresis and the areas of the individual peaks were calculated using standard methods. As can be seen in the chromatographs and quantitated data, the second sample, which was treated with fumed silica prior to filtration, resulted in a filtrate with a much higher IgG purity than the sample not treated with fumed silica (68.8% vs. 55.7 γ-globulin; compare Table 18 with Table 16).

TABLE 17

Figure 7A:
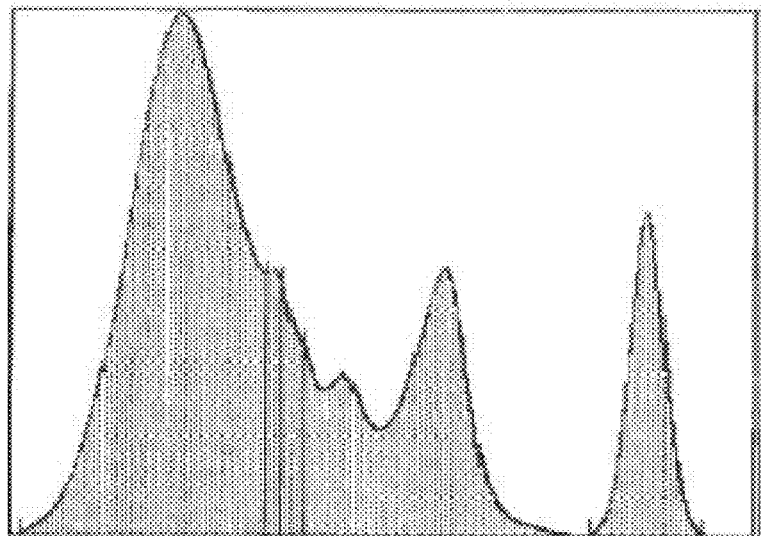
FIG. 7: Difference in purity of the modified fraction II+III filtrate with and without fumed silica treatment. Chromatograph of cellulose acetate electrophoresis of modified fraction II+III filtrate (A) clarified by filter aid only and (B) clarified after fumed silica treatment.
Figure 7B:
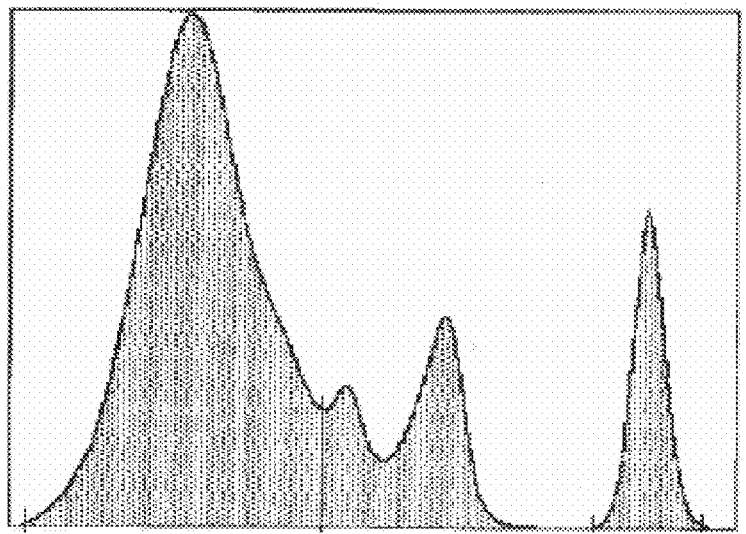

Quantitation of protein peaks separated by cellulose acetate electrophoresis from the Fraction II + III suspension clarified by addition of filter aid only prior to filtration, shown in FIG. 7A.

| number of peak from left to right | area (%) | fraction |
|---|---|---|
| 1 | 55.7 | γ-globulin |
| 2 | 3.2 | denatured protein |
| 3 | 3.7 | γ-globulin |
| 4 | 25.5 | α/β-globulin |
| 5 | 11.9 | albumin |

TABLE 18

Quantitation of protein peaks separated by cellulose acetate electrophoresis from the Fraction II + III suspension pretreated with fumed silica and clarified by addition of filter aid prior to filtration, shown in FIG. 7B.

| number of peak from left to right | area (%) | fraction |
|---|---|---|
| 1 | 68.3 | γ-globulin |
| 2 | 18.9 | α/β-globulin |
| 3 | 12.3 | albumin |

Example 18

The present example illustrates ultrafiltration and formulation of a 20% IgG preparation suitable for subcutaneous administration. This information was gathered during production of scale-up and pre-clinical 20% IgG preparations. The process used for manufacturing of 20% lots prior to the nanofiltration step was as described above. Ultra-/diafiltration was improved to concentrate the solution to 20%. In order to reduce yield loss to a minimum, the post-wash of the ultrafiltration device used for diafiltration is concentrated by a second smaller device equipped with the same membranes and afterwards added to the bulk solution.

Surprisingly it could be shown that virus inactivation during low pH storage is not influenced by the protein concentration of the solution. Similar virus reduction was achieved in both 10% solution (GAMMAGARD® LIQUID) and in 20% solution. Therefore low pH storage as a virus reduction step was maintained for the 20% product.

Prior to nanofiltration, the glycine concentration of the IgG solution is adjusted to a target of 0.25M. The solution is then concentrated to a protein concentration of 6±2% w/v through ultrafiltration (UF). The pH is adjusted to 5.2±0.2. The UF membrane used has a Nominal Molecular Weight Cut Off (NMWCO) of 50,000 daltons or less and is especially designed for high viscosity products (e.g., V screen from Millipore).

The concentrate is then diafiltered against a 0.25M glycine solution, pH 4.2±0.2. The minimum exchange volume is 10 times the original concentrate volume. Throughout the ultrafiltration/diafiltration operation, the solution is maintained at between about 4° C. to 20° C.

After diafiltration, the solution is concentrated to a protein concentration of at least 22% (w/v). The solution temperature is adjusted to 2° C. to 8° C.

In order to recover the complete residual protein in the system, the post-wash of the first bigger ultrafiltration system is done with at least 2 times the dead volume in re-circulation mode to assure that all protein is washed out. Then the post-wash of the first ultrafiltration system is concentrated to a protein concentration of at least 22% w/v with a second ultra-/diafiltration system equipped with the same type of membrane which is dimensioned a tenth or less of the first one. The post-wash concentrate is added to the bulk solution. The second ultrafiltration system is then post-washed. This post-wash is used for adjustment of the protein concentration of the final formulation. The solution temperature is maintained at between about 2° C. to 8° C.

In order to formulate the final solution, the protein concentration is adjusted to about 20.4±0.4% (w/v) with post-wash of the second smaller ultrafiltration system and/or with diafiltration buffer. The pH is adjusted to between about 4.4 to 4.9, if necessary.

Example 19

In order to compare the fraction of IgG recovered in the Fraction II+III filtrate in the current GAMMAGARD® LIQUID manufacturing process, five manufacturing scale purifications of IgG were performed using the improved Fraction II+III precipitation and dissolution methods provided herein. Briefly, precipitation of IgG Cohn pools with a starting IgG concentration of about 6.14 g/L was performed at −7° C. with 25% ethanol incorporated by fluent addition, as compared to −5° C. and 20% ethanol, as employed in the current manufacturing process. The modified Fraction II+III precipitate was then extracted 1 to 15 with a dissolution buffer having a pH of 4.3 or adjusted with 0.06% glacial acetic acid, and subsequently filtered through a depth filter with a final wash of 4.3 dead filter volumes of dissolution buffer. As seen in Table 18, modified Fraction II+III filtrate prepared according to the improved methods provided herein contained a significantly higher percentage (at least an 8.0% increase) of the IgG present in the starting Cohn pool than did Fraction II+III filtrate prepared according to the present manufacturing procedure (91.1% and 91.6% vs. 83.1% and 83.8%, respectively).

TABLE 18

Average recovery of IgG in the Fraction II + III filtrate of all Baxter manufacturing runs performed in Vienna during 2008 and part of 2009, as compared to IgG recovery in lots manufactured according to the improved methods provided herein.

| | Vienna Manufacturing | | | |
|---|---|---|---|---|
| Process | current | 2008 | R&D Scale-up** | |
| IgG in Cohn pool (g/L) | 6.26 | 6.31 | 6.14 | 6.13 |
| Alcohol at II + III precip. (%) | 20 | 20 | 25 | 25 |
| mL acetic acid/1000 L of dissolution buffer | 510 | 510 | Dissolution at pH 4.3; shift to 4.9 prior filtration | 600 |
| Aerosil (g/g paste) | 0.045 | 0.04 | 0.04 | 0.04 |
| Post-wash in filter press dead volumes | 1.8 | 1.8 | 4.3 | 4.3 |

TABLE 18-continued

Average recovery of IgG in the Fraction II + III filtrate of all Baxter manufacturing runs performed in Vienna during 2008 and part of 2009, as compared to IgG recovery in lots manufactured according to the improved methods provided herein.

| | Vienna Manufacturing | | | |
|---|---|---|---|---|
| Process | current | 2008 | R&D Scale-up** | |
| Average IgG in filtrate (% of Cohn pool) | 83.1% 57 Lots | 83.8% 200 Lots | 91.1% 3 Lots | 91.6% 2 Lots |
| Additional IgG in the filtrate | n.a. | n.a. | +8.0% | +8.5% |

Example 20

In order to determine the purity of the IgG compositions provided herein, three lots of IgG were prepared according to the improved methods provided herein. The final IgG products of these purifications were then tested for several contaminants, including IgA, IgM, Amidolytic activity, C3, and fibrinogen, as well as to determine the percentage of IgG monomers/dimers in the final composition. As can be seen in Table 19 below, the improve methods manufacture provided herein result in final bulk compositions with increased IgG recovery, 73.6% to 78.5% of the starting material as compared to 60% to 70% for currently employed methods, while maintaining purity profiles that are as good, if not better, than current IgG manufacturing standards.

TABLE 19

Levels of impurities and IgG monomer/dimmer composition in IgG composition prepared according to the improved manufacturing methods provided herein.

| Option | 1 | 3 | 6 |
|---|---|---|---|
| Experiment # (P0 ... 10NG2) | 19 | 20 | 21 |
| Protein yield in ANX flow-through [g/L plasma] | 4.35 | 4.35 | 4.38 |
| IgG recovery: Cohn starting material to bulk [%] | 73.6 | 78.5 | 78.5 |
| Characterization of final bulk | | | |
| IgA [µg/mL @10% protein] | 29 | 26 | pend. |
| IgM [µg/mL @10% protein] | 1.1 | 1.1 | pend. |
| Amidolytic activity [PL-1 nmol/mL min] | pend. | <10 | <10 |
| MSD monomers/dimers [%] | 99.7 | 99.9 | 99.7 |
| C3 [µg/mL @10% protein] | pend. | pend. | pend. |
| Fibrogen [µg/mL @10% protein] | <0.2 | pend. | pend. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an enriched IgG composition from plasma, the method comprising the steps of:
   (a) precipitating a cryo-poor plasma fraction, in a first precipitation step, with from about 6% to about 10% alcohol at a pH of from about 7.0 to about 7.5 to obtain a first precipitate and a first supernatant;
   (b) precipitating IgG from the first supernatant, in a second precipitation step, with from about 23% to about 27% alcohol at a pH of from about 6.7 to about 7.1 at a temperature of from −7° C. to −9° C. to form a second precipitate;
   (c) suspending the second precipitate to form a suspension;
   (d) precipitating IgG from the suspension formed in step (c), in a third precipitation step, with from 22% to 28% alcohol at a pH of from 6.7 to 7.3 to form a third precipitate;
   (e) re-suspending the third precipitate to form a suspension; and
   (f) separating the soluble fraction from the suspension formed in step (e), thereby forming an enriched IgG composition.

2. The method of claim 1, wherein the temperature of precipitation step (b) is −7° C.

3. The method of claim 1, wherein the alcohol concentration of precipitation step (b) is about 25%.

4. The method of claim 2, wherein the alcohol concentration of precipitation step (b) is about 25%.

5. The method of claim 1, wherein at least one of the first precipitation step, second precipitation step, or third precipitation step comprises spray addition of the alcohol, the spray addition in the form of fine droplets or mist of the alcohol.

6. The method of claim 1, wherein the first precipitation step, second precipitation step, and third precipitation step comprise spray addition of the alcohol, the spray addition in the form of fine droplets or mist of the alcohol.

7. The method of claim 1, wherein the pH of at least one of the first precipitation step, second precipitation step, or third precipitation step is achieved by addition of a pH modifying solution after addition of the alcohol.

8. The method of claim 7, wherein the addition of a pH modifying solution comprises spray addition of the pH modifying solution.

9. The method of claim 1, wherein the pH of all of the first precipitation step, second precipitation step, and third precipitation step is achieved by addition of a pH modifying solution after addition of the alcohol.

10. The method of claim 9, wherein the addition of a pH modifying solution comprises spray addition of the pH modifying solution.

11. The method of claim 1, wherein the pH of the precipitation step is modified before and after the addition of alcohol, during and after the addition of alcohol, or before, during, and after the addition of alcohol.

12. The method of claim 1, wherein the pH of at least one precipitation step is maintained for the entire precipitation step by continuous adjustment of the pH.

13. The method of claim 1, wherein the precipitate formed in step (b) is suspended with from about 12 L to about 18 L of buffer per kg precipitate.

14. The method of claim 1, wherein the precipitate formed in step (b) is suspended with about 15 L of buffer per kg precipitate.

15. The method of claim 1, wherein the suspension formed in step (c) is treated with finely divided silicon dioxide.

16. The method of claim 15, wherein the suspension formed in step (c) is treated with from about 0.02 kg to about 0.06 kg of finely divided silicon dioxide per kg of the second precipitate suspended.

17. The method of claim 15, wherein treatment with finely divided silicon dioxide comprises mixing the finely divided silicon dioxide with the suspension formed in step (c) for at least 30 minutes.

18. The method of claim 17, wherein the suspension formed in step (c) is treated with from about 0.02 kg to about 0.06 kg of finely divided silicon dioxide per kg of the second precipitate suspended.

19. The method of claim 1, wherein the method further comprises an ion exchange chromatography purification step.

20. The method of claim 1, wherein the method further comprises a nanofiltration step.

21. The method of claim 20, wherein the nanofiltration step comprises the use of a nanofilter having a mean pore size of about 35 nm.

22. The method of claim 1, wherein the enriched IgG composition obtained in step (f) contains at least 85% of the IgG content found in the cryo-poor plasma fraction used in step (a).

23. The method of claim 1, wherein the enriched IgG composition obtained in step (f) contains at least 90% of the IgG content found in the cryo-poor plasma fraction used in step (a).

24. The method of claim 1, wherein the purity of IgG in the final composition is at least 95%.

25. The method of claim 1, wherein the purity of IgG in the final composition is at least 98%.

26. The method of claim 1, wherein the purity of IgG in the final IgG composition is at least 99%.

27. The method of claim 1, wherein the plasma is human plasma.

* * * * *